US012636077B2

(12) United States Patent
Keyes et al.

(10) Patent No.: US 12,636,077 B2
(45) Date of Patent: May 26, 2026

(54) BASKET ASSEMBLY, SPINES, AND ELECTRODES FOR A CATHETER, AND METHODS OF THE SAME

(71) Applicant: Biosense Webster (Israel) Ltd., Yokneam (IL)

(72) Inventors: Joseph Thomas Keyes, Sierra Madre, CA (US); Nathaniel Jenkins, Irvine, CA (US); Kevin Justin Herrera, West Covina, CA (US); Athanassios Papaioannou, Irvine, CA (US); Christopher Thomas Beeckler, Brea, CA (US); Kevin Mark Okarski, Monrovia, CA (US); Ishan Khan, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 434 days.

(21) Appl. No.: 18/499,968

(22) Filed: Nov. 1, 2023

(65) Prior Publication Data

US 2024/0180614 A1    Jun. 6, 2024

Related U.S. Application Data

(60) Provisional application No. 63/385,741, filed on Dec. 1, 2022.

(51) Int. Cl.
*A61B 18/00*     (2006.01)
*A61B 18/14*     (2006.01)

(52) U.S. Cl.
CPC ..................... *A61B 18/1492* (2013.01); *A61B 2018/00267* (2013.01); *A61B 2018/00351* (2013.01); *A61B 2018/00577* (2013.01); *A61B 2018/00613* (2013.01); *A61B 2018/1475* (2013.01)

(58) Field of Classification Search
None
See application file for complete search history.

(56) References Cited

U.S. PATENT DOCUMENTS

| | | | |
|---|---|---|---|
| 4,699,147 A | 10/1987 | Chilson et al. | |
| 4,940,064 A | 7/1990 | Desai | |
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |

(Continued)

FOREIGN PATENT DOCUMENTS

| | | |
|---|---|---|
| CN | 111248993 A | 6/2020 |
| CN | 111248996 A | 6/2020 |

(Continued)

OTHER PUBLICATIONS

Extended European Search Report dated Jul. 16, 2024, from corresponding European Application No. 23213338.9.

*Primary Examiner* — Linda C Dvorak
*Assistant Examiner* — Nicholas S Borsch

(57) ABSTRACT

The disclosed technology includes a spine member for an end effector, the spine member extending along a longitudinal axis from a proximal end to a distal end. The spine member includes a unidirectional proximal stop member to allow an electrode to slide in a direction distally but not proximally and a distal stop member to prevent an electrode from sliding past.

19 Claims, 23 Drawing Sheets

(56)  References Cited

U.S. PATENT DOCUMENTS

| | | | |
|---|---|---|---|
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,391,199 A | 2/1995 | Ben-Haim |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,443,489 A | 8/1995 | Ben-Haim |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,558,091 A | 9/1996 | Acker et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,172,499 B1 | 1/2001 | Ashe |
| 6,216,043 B1 | 4/2001 | Swanson et al. |
| 6,216,044 B1 | 4/2001 | Kordis |
| 6,239,724 B1 | 5/2001 | Doron et al. |
| 6,332,089 B1 | 12/2001 | Acker et al. |
| 6,428,537 B1 | 8/2002 | Swanson et al. |
| 6,456,864 B1 | 9/2002 | Swanson et al. |
| 6,484,118 B1 | 11/2002 | Govari |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,618,612 B1 | 9/2003 | Acker et al. |
| 6,690,963 B2 | 2/2004 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,788,967 B2 | 9/2004 | Ben-Haim et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| 7,536,218 B2 | 5/2009 | Govari et al. |
| RE41,334 E | 5/2010 | Beatty et al. |
| 7,756,576 B2 | 7/2010 | Levin |
| 7,846,157 B2 | 12/2010 | Kozel |
| 7,848,787 B2 | 12/2010 | Osadchy |
| 7,869,865 B2 | 1/2011 | Govari et al. |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,456,182 B2 | 6/2013 | Bar-Tal et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,330,742 B2 | 6/2019 | Govari |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |

(56) References Cited

U.S. PATENT DOCUMENTS

| | | |
|---|---|---|
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 11,304,642 B2 | 4/2022 | Govari et al. |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1* | 11/2013 | Madjarov .......... A61B 18/1492 606/41 |
| 2014/0025069 A1 | 1/2014 | Willard et al. |
| 2014/0052118 A1 | 2/2014 | Laske et al. |
| 2014/0114304 A1* | 4/2014 | Wang ................. A61B 18/1492 606/41 |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0303546 A1 | 10/2018 | Buysman et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |

(56)                References Cited

U.S. PATENT DOCUMENTS

| | | |
|---|---|---|
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0155224 A1 | 5/2020 | Bar-Tal |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altmann et al. |
| 2021/0162210 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |
| 2022/0361942 A1 | 11/2022 | Lichter et al. |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3181082 A1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| EP | 4215143 A1 | 7/2023 |
| EP | 4268750 A1 | 11/2023 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020206328 A1 | 10/2020 |

* cited by examiner

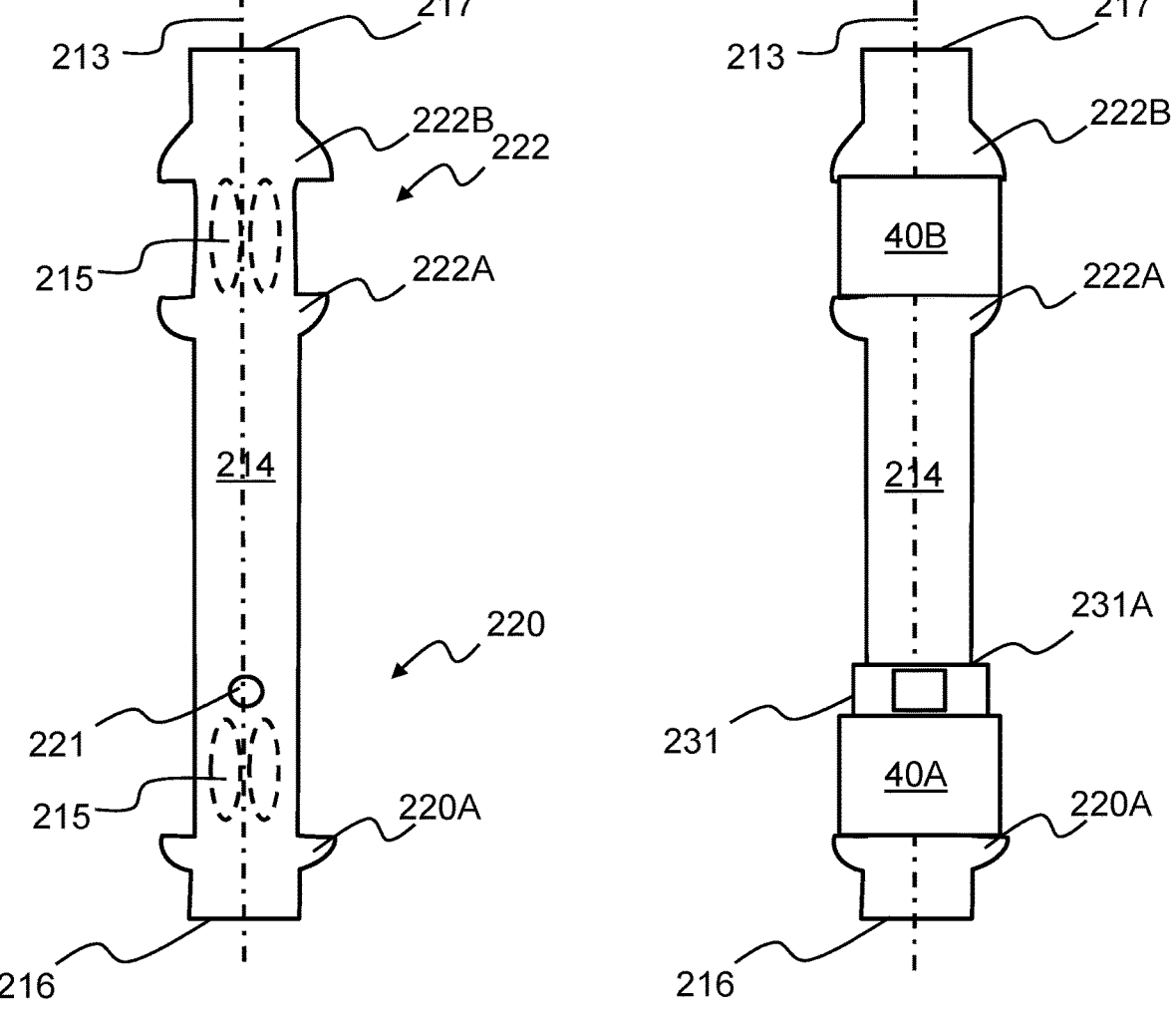
FIG. 11A                    FIG. 11B

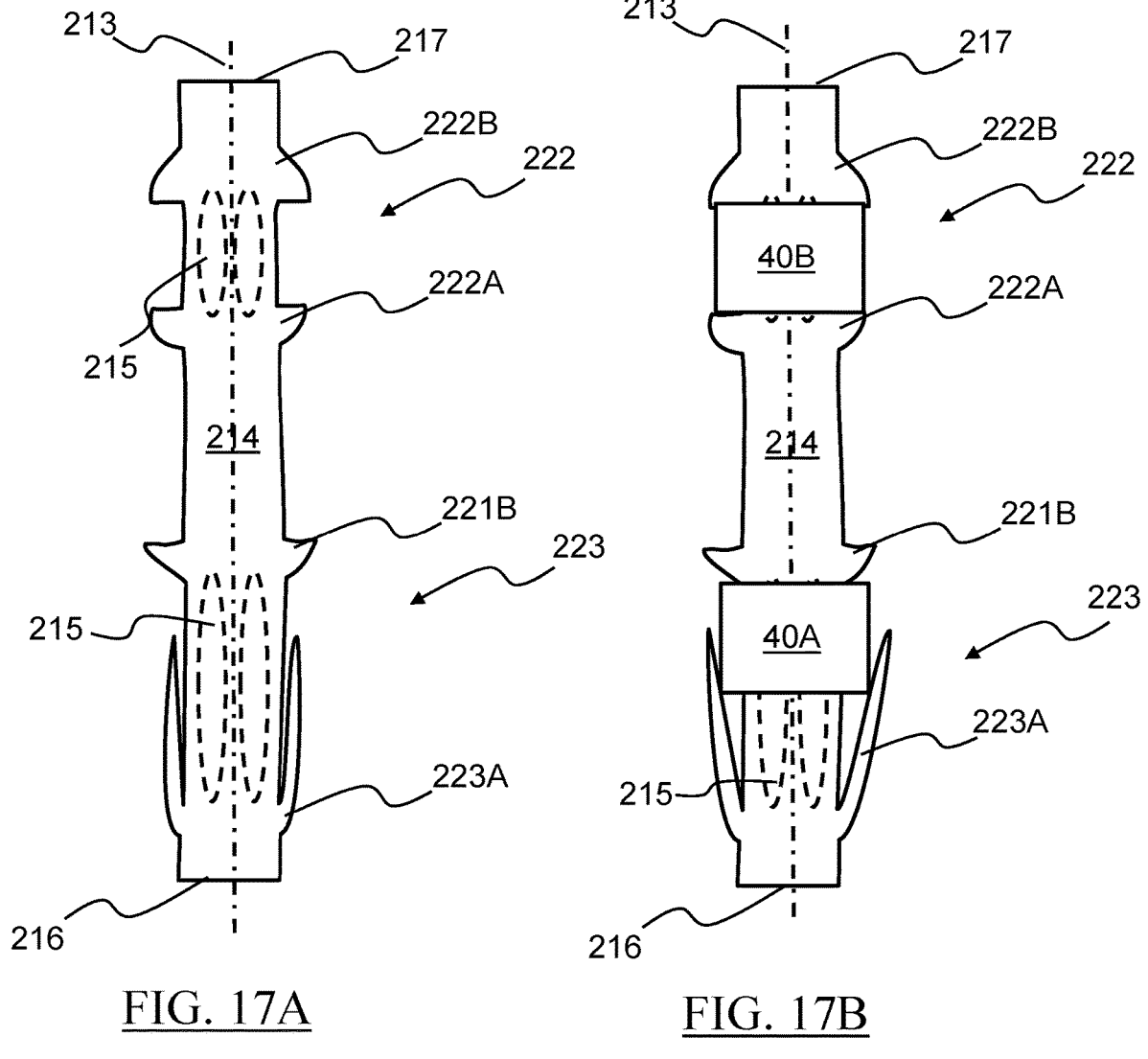
FIG. 17A                    FIG. 17B

2000

Start

2002 Aligning a spine with an electrode

2004 Inserting the spine into a lumen of the electrode

2006 Aligning a locking stub of the electrode with the aperture of the spine

2008 Crimping the electrode onto the spine such that the locking stub extends at least partially into the aperture End

2100

2102

2104

2106

BASKET ASSEMBLY, SPINES, AND ELECTRODES FOR A CATHETER, AND METHODS OF THE SAME

FIELD

This application claims, under 35 U.S.C. § 119(e), priority to and the benefit of U.S. Provisional Patent Application No. 63/385,741, filed Dec. 1, 2022, the entire contents of which are incorporated herein by reference.

FIELD

The present invention relates generally to medical devices, and in particular catheters with electrodes, and further relates to, but not exclusively, catheters suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art utilize radiofrequency (RF) electrical energy to heat tissue. RF ablation can have certain risks related to thermal heating which can lead to tissue charring, burning, steam pop, phrenic nerve palsy, pulmonary vein stenosis, and esophageal fistula.

Cryoablation is an alternative approach to RF ablation that generally reduces thermal risks associated with RF ablation. Maneuvering cryoablation devices and selectively applying cryoablation, however, is generally more challenging compared to RF ablation; therefore cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference and attached in the Appendix hereto.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Due to the small size of the spines and the electrodes, however, soldering, welding, or adhering the electrodes to the spines can be a difficult task, increasing the manufacturing time and cost and the chances that the electrode fails due to an improper bond or misalignment.

What is needed, therefore, are systems and methods of attaching an electrode to a spine of a basket assembly without the need for soldering, welding, or using adhesive.

SUMMARY

There is provided, in accordance with an example of the present invention, a spine member for an end effector for an expendable basket assembly for a medical probe. The spine member may extend along a longitudinal axis from a proximal end to a distal end. The spine member may include a unidirectional proximal stop member to allow an electrode to slide in a direction distally but not proximally and a distal stop to prevent an electrode from sliding past. In this way, the presently disclosed technology can be used to secure the electrodes to the spines without requiring solder, weld, or adhesives.

There is provided, in accordance with an example of the present invention, an expandable basket assembly for a medical probe. The expandable basket assembly may include a plurality of spines configured to bow radially outward from a central axis when the expandable basket assembly is transitioned from a collapsed form to an expanded form. Each spine of the plurality of spines may include (i) a proximal electrode stop configured to allow a distal electrode to slide distally on each spine past the proximal electrode stop but prevent a proximal electrode from sliding distally past the proximal electrode stop and (ii) a distal electrode stop configured to prevent the distal electrode from sliding distally past the distal electrode stop.

The proximal electrode stop may include a pair of first proximal protrusions extending from opposing sides of each spine with a first proximal facing portion angled away from a proximal end of each spine and a first distal facing portion approximately parallel with the proximal end of each spine.

The proximal electrode stop may also include a pair of second proximal protrusions extending from the opposing sides of each spine with second proximal facing portion angled away from the proximal end of each spine.

The proximal electrode stop may include a bulged portion in a default state that is configured to retain an electrode in place in a default state and configured to allow an electrode to travel distally along each spine when the respective spine is deformed.

The proximal electrode stop may include a first pair of lateral cutouts, a second pair of lateral cutouts, a first coil, and a second coil. The first pair of lateral cutouts may be configured to receive the first coil and the second pair of lateral cutouts may be configured to receive the second coil. The first and second coils may be configured to restrain the proximal electrode positioned therebetween from sliding distally or proximally after the distal electrode is positioned distally past the proximal electrode stop.

The distal electrode stop may include a third pair of lateral cutouts, a fourth pair of lateral cutouts, and a third coil, a fourth coil. The third pair of lateral cutouts may be configured to receive the third coil and the fourth pair of lateral cutouts configured to receive the fourth coil. The third and fourth coils may be configured to restrain the distal electrode positioned therebetween from sliding distally or proximally.

The proximal electrode stop may include a proximal diamond portion, a distal diamond portion, and a diamond intersection connected to the proximal and distal diamond portions.

In a default state, the proximal diamond portion may be configured to prevent the proximal electrode from sliding proximally. In the default state, the distal diamond portion may be configured to prevent the proximal electrode from sliding distally.

In an expanded state, the proximal diamond portion is configured to allow the distal electrode to slide distally. Also in the expanded state, the distal diamond portion is configured to allow the distal electrode to slide distally.

The proximal electrode stop may include a pair of proximal protrusions. The pair of proximal protrusions may include a proximal face angled away from the proximal end of the spine and a distal face substantially parallel to the proximal end of the spine. The proximal electrode stop may also include a distal aperture configured to receive a protrusion of a retainer rivet.

The retainer rivet may include a polymer.

The proximal electrode stop may include a shim distal to the pair of first proximal protrusions that is configured to insert into a lumen of the proximal electrode and prevent distal movement of the proximal electrode.

The proximal electrode stop may include a first shim that is configured to insert into a lumen of the proximal electrode and prevent proximal movement of the proximal electrode. The proximal electrode may also include a second shim distal to the pair of first proximal protrusions that is configured to insert into the lumen of the proximal electrode and prevent distal movement of the proximal electrode.

The proximal electrode stop may include a pair of first proximal protrusions extending from opposing sides of each spine with a first proximal facing portion angled away from a proximal end of each spine and a first distal facing portion approximately perpendicular with the proximal end of each spine. The distal electrode stop may include a pair of distal protrusions extending from opposing sides of each spine with a proximal facing portion substantially perpendicular with the proximal end of each spine.

The expandable basket assembly may include a flexible member between the proximal electrode and the distal electrode.

The flexible member may be configured to prevent proximal movement of the distal electrode and distal movement of the proximal electrode.

Each spine may include a first width at the proximal electrode stop and second width at the distal electrode stop. The second width may be greater than the first width.

Each spine may gradually change from the first width to the second width.

The proximal electrode may include a first lumen with a first diameter less than or equal to the first width such that it cannot move distally past the proximal electrode stop. The distal electrode may include a second lumen with a second diameter greater than the first width but less than or equal to the second width such that it cannot move distally past the distal electrode stop when placed on each spine.

The expandable basket assembly may include the proximal electrode that may include a first lumen gradually changing from a first diameter to a second diameter. The first diameter may be less than or equal to the first width and the second diameter may be greater than the first diameter and less than or equal to the second width. The distal electrode may have a second lumen gradually changing from the second diameter to the first diameter.

Each spine may include (i) a first width at the proximal end for a first length extending away from the proximal end and (ii) a second width for a second length. The second width may be greater than the first width. Each spine may also include a third width for a third length and the third width may be greater than the second width. The first width may gradually increase to the second width over a fourth length and the second width may gradually increase to the third width over a fifth length.

The proximal electrode stop may a pair of first proximal arms extending from opposing sides of each spine angled away from the proximal end of each spine, the pair of arms are configured to close such that the distal electrode can slide over the pair of arms while also forming a pocket retaining the proximal electrode when the proximal electrode moves proximally.

Each spine may include (i) a first portion configured to receive and connect with the proximal electrode and having a first width, (ii) a second portion having a second width, and (iii) a third portion having a third width and configured to receive and connect with the distal electrode. The second width may be greater than the first and third width.

Each spine of the plurality of spines may include one or more apertures extending therethrough from a first side of the spine to a second side of the spine. The one or more apertures configured to receive a locking stub of the proximal or distal electrode such that when the proximal or distal electrode is mechanically coupled to the spine, the locking stub may extend through the aperture preventing the proximal and distal electrode from sliding distally or proximally along the spine.

The proximal and distal electrodes may each define a lumen extending therethrough and a locking stub extending at least partially into the lumen.

Each spine of the plurality of spines may pass through a lumen of the proximal and distal electrodes.

There is provided, in accordance with an example of the present invention, an expandable basket assembly for a medical probe. The expandable basket assembly may include a plurality of electrodes and a plurality of spines configured to bow radially outward from a central axis when the expandable basket assembly is transitioned from a collapsed form to an expanded form. Each spine of the plurality of spines may include a plurality of electrode extension portions extending radially from each spine. Each electrode extension portion may include a band to receive and retain an electrode of the plurality of electrodes.

The plurality of electrodes may include platinum.

The plurality of electrode extension portions may include an adjustable height.

There is provided, in accordance with an example of the present invention, a method of constructing a medical probe. The method may include aligning a spine of an expandable basket assembly with an electrode of the expandable basket assembly, the spine comprising a proximal end, a distal end, and an aperture extending therethrough. The method may also include inserting the spine into a lumen of the electrode and aligning a locking stub of the electrode with the aperture. The method may also include crimping the electrode onto the spine such that the locking stub extends at least partially into the aperture to prevent the electrode from sliding proximally or distally along the spine.

The spine may also include an insulative material configured to electrically isolate the spine from the electrode.

The expandable basket assembly may include an insulative material disposed between the electrode and the spine to electrically isolate the electrode from the spine.

The lumen may include a first lumen. The method may also include (i) aligning an electrically conductive member of the medical probe with a second lumen of the electrode, (ii) inserting the electrically conductive member into the second lumen, and (iii) coupling the electrically conductive member to the electrode such that the electrically conductive member is in electrical communication with the electrode.

The electrically conductive member may be insulated from the spine.

An interface between the locking stub of the electrode and the spine at the aperture comprises an interference fitting.

The spine may include a material selected from a group consisting of nitinol, cobalt chromium, stainless steel, titanium.

The spine may include a polymer material.

The aperture of the spine comprises a first aperture. The spine may include a second aperture. The method may further include (i) aligning the spine with a second electrode of the expandable basket assembly, (ii) inserting the spine into a lumen of the second electrode, (iii) aligning a locking stub of the second electrode with the second aperture, and (iv) crimping the second electrode onto the spine such that the locking stub extends at least partially into the second aperture to prevent the second electrode from sliding proximally or distally along the spine.

There is provided, in accordance with an example of the present invention, a method of constructing a medical probe. The method may include (i) sliding a distal electrode from a proximal end of a spine past a proximal electrode position, (ii) sliding a proximal electrode from the proximal end to the proximal electrode position, and (iii) securing the proximal and distal electrode to the spine.

BRIEF DESCRIPTION OF THE DRAWINGS

FIG. 4A is a schematic pictorial illustration showing a front perspective view of an electrode before being crimped while

FIG. 5A is a schematic pictorial illustration showing a side perspective view of an electrode before being crimped while FIG. 5B is a schematic pictorial illustration showing a side perspective view of an electrode after being crimped, in accordance with an embodiment of the present invention;

FIG. 6A is a schematic pictorial illustration showing a front perspective view of an electrode and a spine before the electrode is crimped to the spine while

FIG. 11A is a top view of a spine with an electrode stop having a distal aperture, in accordance with embodiments of the present invention;

FIG. 11B is a top view of the spine of FIG. 11A with a retainer rivet and electrodes, in accordance with embodiments of the present invention;

FIG. 17A is a top view of a spine with a proximal electrode stop including proximal arms, in accordance with embodiments of the present invention;

FIG. 17B is a top view of the spine of FIG. 17A with electrodes, in accordance with embodiments of the present invention;

DETAILED DESCRIPTION

Figure 1:
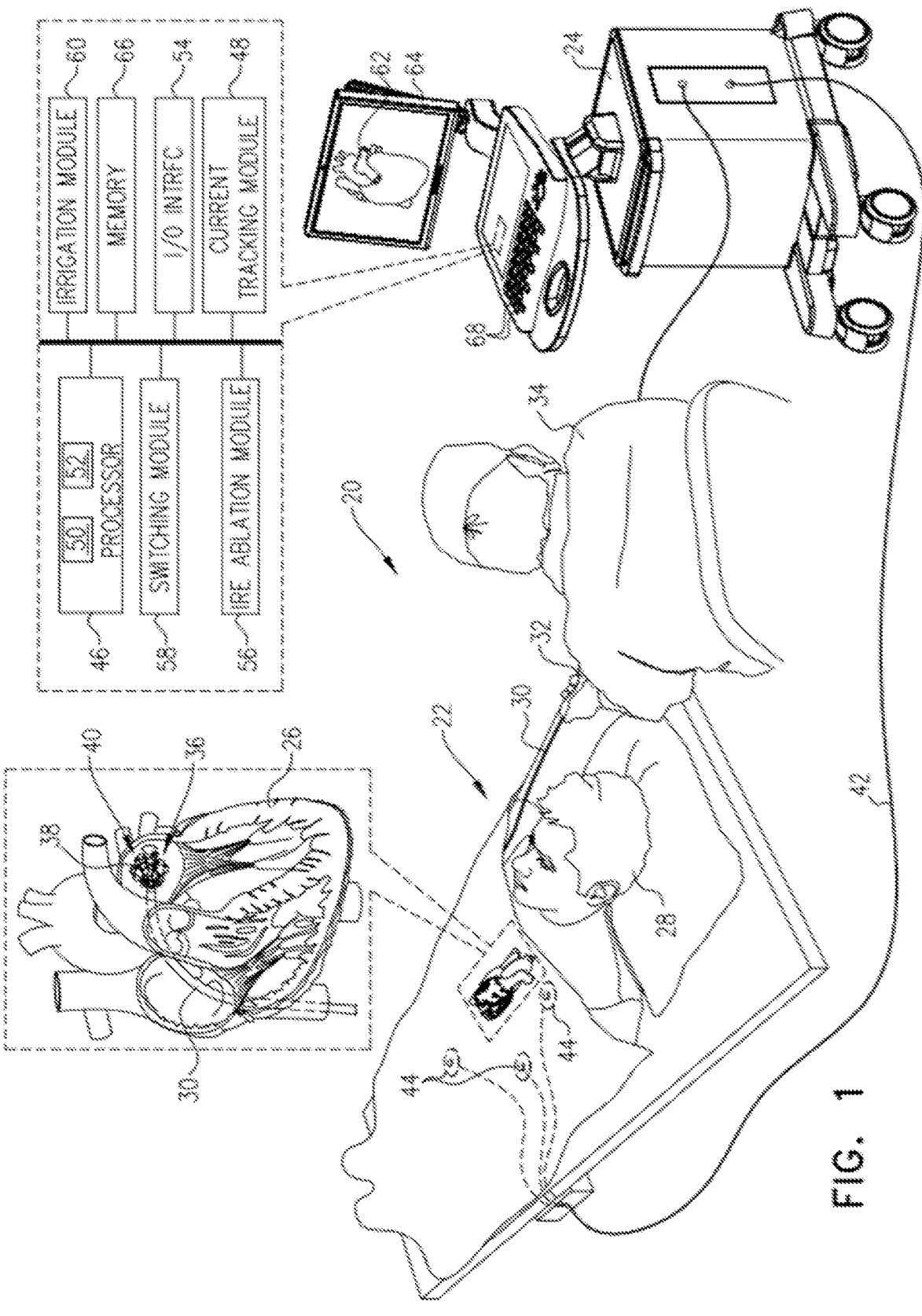
FIG. 1 is a schematic pictorial illustration of a medical system including a medical probe whose distal end includes a basket assembly with electrodes, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator or physician whereas "distal" indicates a location further away to the operator or physician.

As discussed herein, vasculature of a "patient," "host." "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), sometimes referred to interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode having a high current density and high electric flux density is positioned at a treatment site, and a second electrode having comparatively lower current density and lower electric flux density is positioned remotely from the treatment site.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The present disclosure is related to systems, method or uses and devices for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation. RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore cryoablation is not viable in certain anatomical geometries which may be reached by electrical ablation devices.

While RF ablation and cryoablation, are based on thermal energy transfer to induce local tissue necrosis, the solution of this disclosure can resolve these and other problems by utilizing irreversible electroporation (IRE), sometimes referred to interchangeably as pulsed electric field (PEF) ablation and pulsed field ablation (PFA). IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by apoptosis. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter electrodes positioned in the vicinity of myocardial tissue to generate a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated herein by reference and attached in the Appendix hereto.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, and 2021/0186604A1, the entireties of each of which are incorporated herein by reference and attached in the Appendix hereto.

To deliver pulsed field ablation (PFA) in an IRE (irreversible electroporation) procedure, electrodes should contact the tissue being ablated with a sufficiently large surface area. As described hereinbelow, the medical probe includes a flexible insertion tube having proximal and distal ends, and a basket assembly at the distal end of the flexible insertion tube. The basket assembly includes at least one spine and a plurality of electrodes, each given electrode having a lumen therethrough fitting a given spine. The electrodes are crimped to the spine and locked in place with a locking stub to prevent the electrodes from sliding proximally or distally along the length of the spine.

FIG. 1 is a schematic, pictorial illustration of a medical system 20 including a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Medical probe 22 includes a flexible insertion tube 30 and a handle 32 coupled to a proximal end of the insertion tube. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy a basket assembly 38 affixed to distal end 36. Basket assembly 38 can include a plurality of electrodes 40 affixed to a plurality of spines, as described in the description referencing FIGS. 2A and 2B hereinbelow. To start performing a medical procedure such as irreversible electroporation (IRE) ablation, medical professional 34 can manipulate handle 32 to position distal end 36 so that electrodes 40 engage cardiac tissue at a desired location or locations. Upon positioning the distal end 36 so that electrodes 40 can engage cardiac tissue, the medical professional 34 can activate the medical probe 22 such that electrical pulses are delivered by the electrodes 40 to perform the IRE ablation.

In the configuration shown in FIG. 1, control console 24 is connected, by a cable 42, to body surface electrodes, which typically include adhesive skin patches 44 that are affixed to patient 28. Control console 24 includes a processor 46 that, in conjunction with a tracking module 48, determines location coordinates of distal end 36 inside heart 26. Location coordinates can be determined based on electromagnetic position sensor output signals provided from the distal portion of the catheter when in the presence of a generated magnetic field. Location coordinates can additionally, or alternatively be based on impedances and/or currents measured between adhesive skin patches 44 and electrodes 40 that are affixed to basket assembly 38. In addition to being used as location sensors during a medical procedure, electrodes 40 may perform other tasks such as ablating tissue in the heart.

As described hereinabove, in conjunction with tracking module 48, processor 46 may determine location coordinates of distal end 36 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are (also) configured to deliver IRE ablation energy to tissue in heart 26, configuring electrodes 40 to deliver any other type of ablation energy to tissue in any body cavity is considered to be within the spirit and scope of the present invention. Furthermore, although described in the context of being electrodes 40 that are configured to deliver IRE ablation energy to tissue in the heart 26, one skilled in the art will appreciate that the disclosed technology can be applicable to electrodes used for mapping and/or determining various characteristics of an organ or other part of the patient's 28 body.

Processor 46 may include real-time noise reduction circuitry 50 typically configured as a field programmable gate array (FPGA), followed by an analog-to-digital (A/D) signal conversion integrated circuit 52. The processor can be programmed to perform one or more algorithms and uses circuitry 50 and circuit 52 as well as features of modules to enable the medical professional 34 to perform the IRE ablation procedure.

Control console 24 also includes an input/output (I/O) communications interface 54 that enables control console 24 to transfer signals from, and/or transfer signals to electrodes 40 and adhesive skin patches 44. In the configuration shown in FIG. 1, control console 24 additionally includes an IRE ablation module 56 and a switching module 58.

IRE ablation module 56 is configured to generate IRE pulses having peak power in the range of tens of kilowatts. In some examples, the electrodes 40 are configured to deliver electrical pulses having a peak voltage of at least 900 volts (V). The medical system 20 performs IRE ablation by delivering IRE pulses to electrodes 40. Preferably, the medical system 20 delivers biphasic pulses between electrodes 40 on the spine. Additionally, or alternatively, the medical system 20 delivers monophasic pulses between at least one of the electrodes 40 and a skin patch.

In order to dissipate the heat and to improve the efficiency of the ablation process, system 20 supplies irrigation fluid (e.g., a saline solution) to distal end 36 via a channel (not shown) in insertion tube 30. Control console 24 includes an irrigation module 60 to monitor and control irrigation parameters, such as the pressure and the temperature of the irrigation fluid.

Based on signals received from electrodes 40 and/or adhesive skin patches 44, processor 46 can generate an electroanatomical map 62 that shows the location of distal end 36 in the patient's body. During the procedure, processor 46 can present map 62 to medical professional 34 on a display 64, and store data representing the electroanatomical map in a memory 66. Memory 66 may include any suitable volatile and/or non-volatile memory, such as random-access memory or a hard disk drive.

In some embodiments, medical professional 34 can manipulate map 62 using one or more input devices 68. In alternative embodiments, display 64 may include a touch-screen that can be configured to accept inputs from medical professional 34, in addition to presenting map 62.

Figures 2A, 2B:
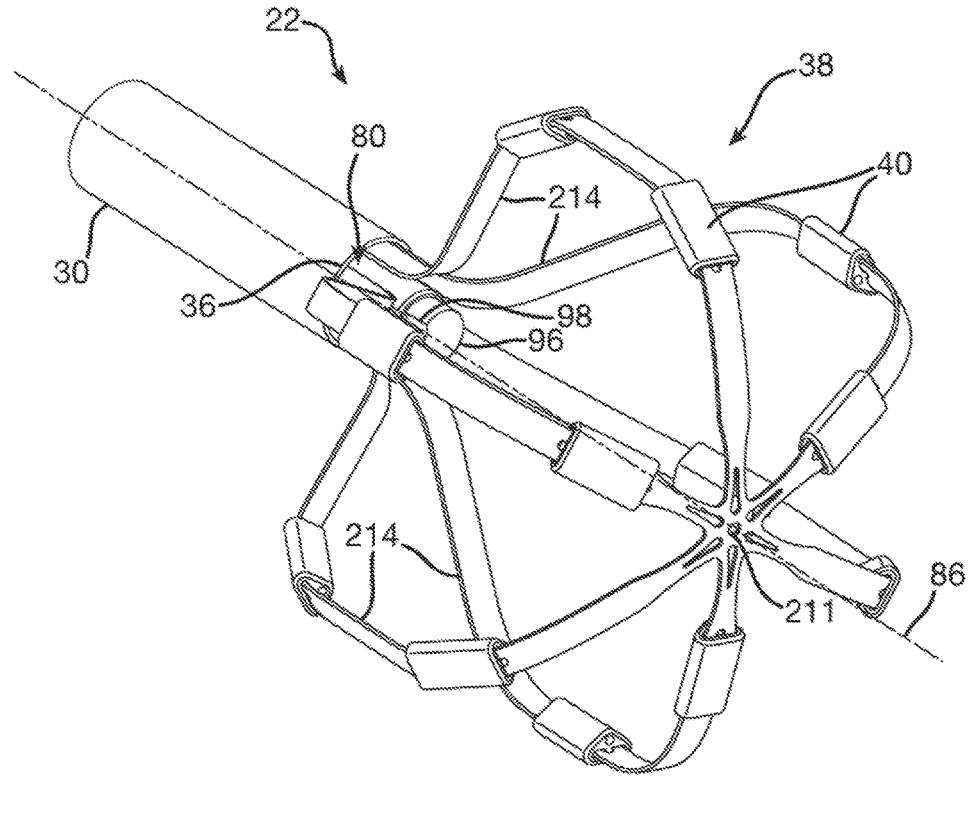
FIG. 2A is a schematic pictorial illustration showing a perspective view of a medical probe in an expanded form, in accordance with an embodiment of the present invention.
FIG. 2B is a schematic pictorial illustration showing a side view of a medical probe in a collapsed form, in accordance with the disclosed technology.

FIG. 2A is a schematic pictorial illustration showing a perspective view of a medical probe 22 having a basket assembly 38 in an expanded form when unconstrained, such as by being advanced out of an insertion tube lumen 80 at a distal end 36 of an insertion tube 30. FIG. 2B shows the basket assembly in a collapsed form within insertion tube 30. In the expanded form (FIG. 2A), the spines 214 bow radially outwardly from a longitudinal axis 86 of the medical probe 22 and in the collapsed form (FIG. 2B) the spines are arranged generally along the longitudinal axis 86 of the medical probe 22.

As shown in FIG. 2A, basket assembly 38 includes a plurality of flexible spines 214 that are formed at the end of a tubular shaft 84 and are connected at both ends. During a medical procedure, medical professional 34 can deploy basket assembly 38 by extending tubular shaft 84 from insertion tube 30 causing the basket assembly 38 to exit the insertion tube and transition to the expanded form. Spines 214 may have elliptical (e.g., circular) or rectangular (that may appear to be flat) cross-sections, and include a flexible, resilient material (e.g., a shape-memory alloy such as nickel-titanium (also known as Nitinol), cobalt chromium, stainless steel, titanium, or any other suitable material or combinations of materials).

In embodiments described herein, electrodes 40 can be configured to deliver ablation energy (RF and/or IRE) to tissue in heart 26. For example, the electrodes 40 can be configured to deliver 20-30 amps of electrical current to cardiac tissue to facilitate ablation of the cardiac tissue. Furthermore, the electrodes 40 can be configured for bipolar or unipolar ablation schemes depending on the particular application. Alternatively, or in addition, the electrodes can be used to determine the location of basket assembly 38 and/or to measure a physiological property such as local surface electrical potentials at respective locations on tissue in heart 26.

Examples of materials ideally suited for forming electrodes 40 include gold, platinum, and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 26.

Basket assembly 38 has a distal end 94 and includes a stem 96 that extends longitudinally from a distal end 36 of shaft 84 towards distal end 94 of basket assembly 38. As described supra, control console 24 includes irrigation module 60 that delivers irrigation fluid to distal end 36. Stem 96 includes multiple spray ports 98, wherein each given spray port 98 can be angled to aim delivery of the irrigation fluid to either a given electrode 40 or to tissue in heart 26.

Since electrodes 40 do not include spray ports that deliver irrigation fluid, the configuration described hereinabove enables heat to be transferred from the tissue (i.e., during an ablation procedure) to the portion of the electrodes 40 on the inner side of the spines 214, and the electrodes 40 can be cooled by aiming the irrigation fluid, via spray ports 98, at the portion of the electrodes 40 on the inner side of the spines 214.

Figures 3A, 3B:
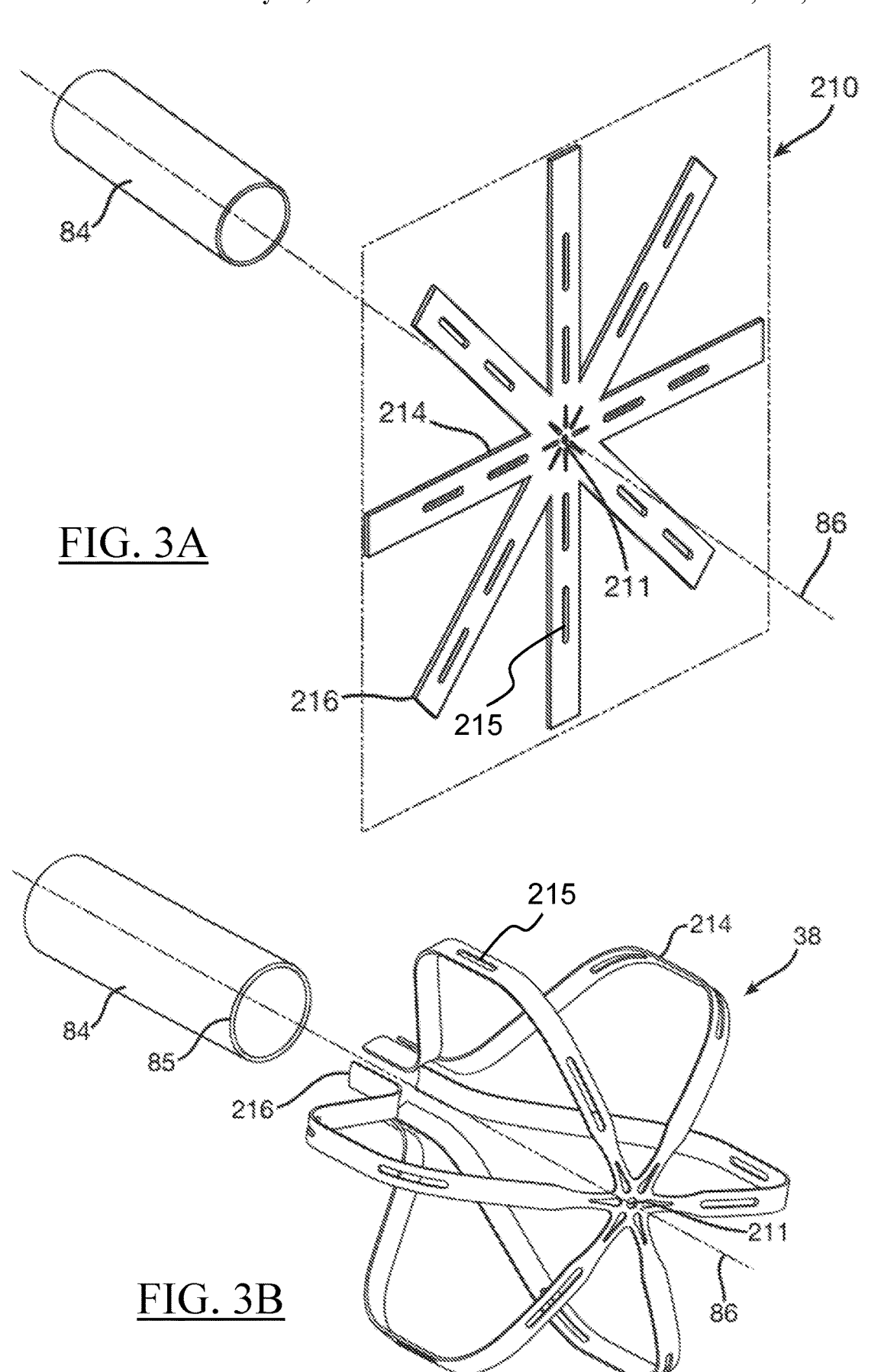
FIGS. 3A and 3B are schematic pictorial illustrations showing exploded views of a tubular shaft and spines of the basket assembly to illustrate how the spines can be assembled together with the tubular shaft, in accordance with an embodiment of the present invention.

FIGS. 3A and 3B are schematic pictorial illustrations showing exploded views of a tubular shaft 84 and spines 214 of the basket assembly 38 to provide one example of how the spines 214 can be assembled together with the tubular shaft 84, in accordance with an embodiment of the present invention. As shown in FIG. 3A, the spines 214 can form a spine assembly 210. The spines 214 can be formed from a single sheet of planar material to form a generally star shape. In other words, the spines 214 can be formed from the single sheet of planar material such that the spines 214 converge toward a central intersection 211. The intersection 211 can be a solid piece of material or include one or more apertures.

The spines 214 can be folded or otherwise bent such that a proximal end 216 of the spines 214 can be inserted into the distal end 85 of the tubular shaft 84 as shown in FIG. 3B. Although not shown in FIGS. 3A and 3B, it will be appreciated that the electrodes 40 can be attached to the spines 214 before the spines are inserted into the tubular shaft 84 to form the basket assembly 38. As stated previously, the spines 214 can include a flexible, resilient material (e.g., a shape-memory alloy such as nickel-titanium, also known as Nitinol) that can enable the basket assembly 38 to transition from its collapsed form (as shown in FIG. 2B) to its expanded form (as shown in FIG. 2A) when the basket assembly 38 is deployed from the insertion tube 30.

The spines 214 can each define an aperture 215 that can be sized and positioned to receive a locking stub 80 of the electrode 40 as will be described in greater detail herein. By receiving the locking stub 80, the aperture 215 can help to prevent the electrode 40 from sliding proximally or distally along the length of the spine 214. In other words, the aperture 215 can help to secure the electrode 40 to the spine 214 when the locking stub 80 extends through the aperture 215, without requiring a weld, a fastener, adhesive, or other fastening devices or methods. As a non-limiting example, the spines 214 can include at least two apertures 215 positioned on a length of the spine 214 between a proximal end of the spine 214 and a distal end of the spine 214. In this way, the basket assembly 38 can have at least two electrodes 40 along each length of spine 214 extending between the proximal end to the distal end of the basket assembly 38 such that the basket assembly 38 can have a total of twelve electrodes. The aperture 215 can be arranged to receive an electrode (e.g., FIGS. 5A, 5B, 6A, 6B, 7A-7D) and retain such electrode via a mechanical lock between the electrode and the spine by virtue of aperture 215.

As will be appreciated by one skilled in the art with the benefit of this disclosure, the basket assembly 38 shown in FIGS. 2A-3B having spines 214 formed from a single sheet of planar material and converging at a central intersection is offered merely for illustrative purposes and the disclosed technology can be applicable to other configurations of basket assemblies 38. For example, the disclosed technology can be applicable to basket assemblies 38 formed from a single spine 214 or multiple spines 214 with each spine 214 being attached at both ends. In other examples, the basket assembly 38 can include a central hub connecting the multiple spines 214 together at a distal end 94 of the basket assembly 38. In yet other examples, the basket assembly 38 can include a single spine 214 configured to form a spiral, multiple spines 214 configured to form a spiral, multiple spines 214 configured to form a tripod or multiple tripods, or any other shape of basket assembly 38. As well, the spine assembly 210 can be formed by laser cutting a cylindrical hollow stock material whereby the laser is mounted for rotation about the longitudinal axis (and translation thereto) of the cylindrical stock while cutting. Thus, although FIGS. 2A-3B illustrate a specific configuration of basket assembly 38, the disclosed technology should not be construed as so limited.

Figure 4A:
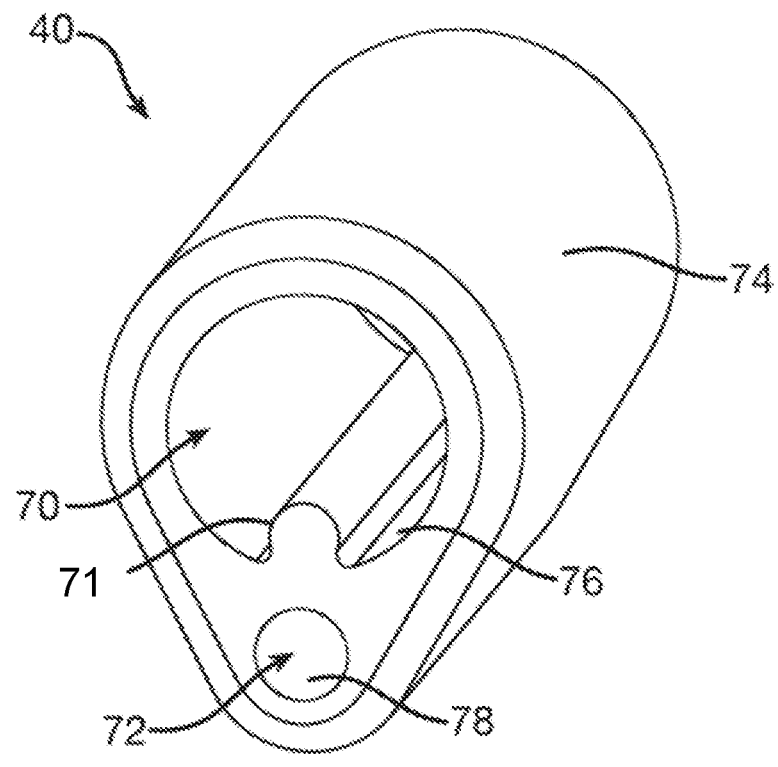
Figure 4B:
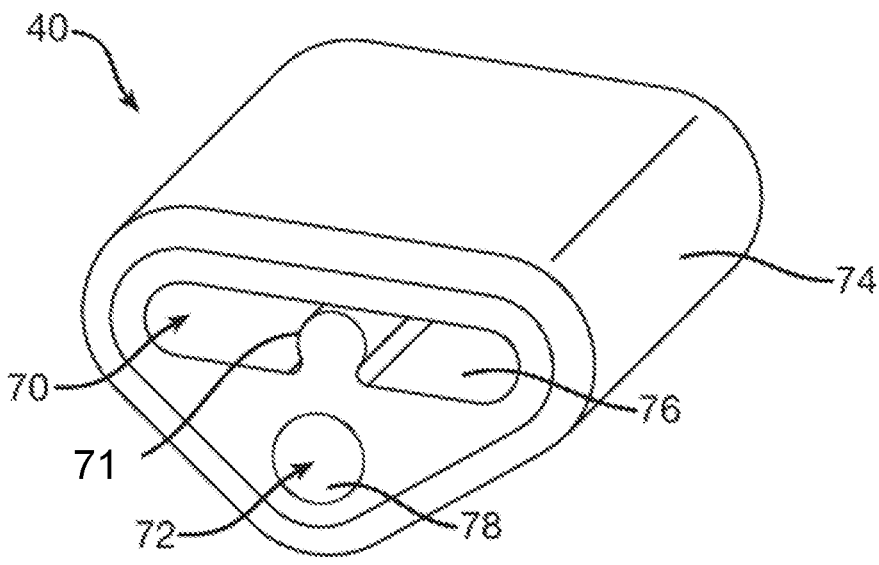
FIG. 4B is a schematic pictorial illustration showing a front perspective view of an electrode after being crimped, in accordance with an embodiment of the present invention.
Figures 5A, 5B:
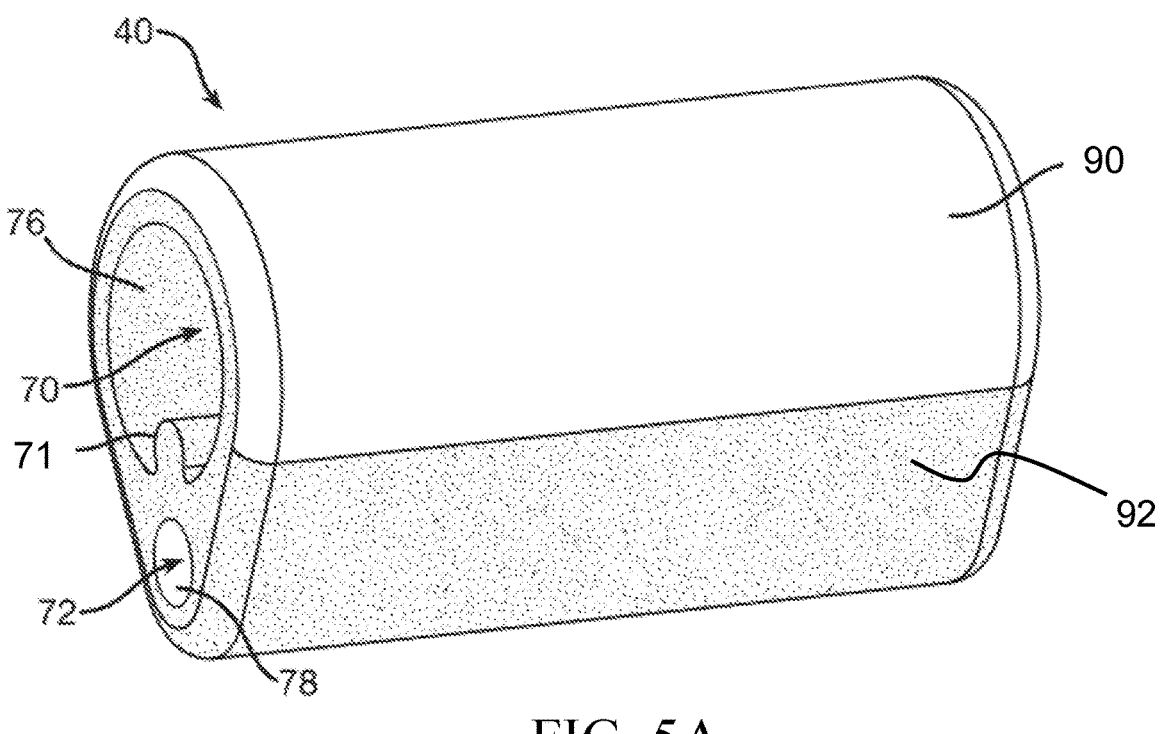

FIG. 4A is a schematic pictorial illustration showing a front perspective view of an electrode 40 before being crimped while FIG. 4B is a schematic pictorial illustration showing a front perspective view of an electrode 40 after being crimped, in accordance with an embodiment of the present invention. Similarly, FIG. 5A is a schematic pictorial illustration showing a side perspective view of an electrode 40 before being crimped while FIG. 5B is a schematic pictorial illustration showing a side perspective view of an electrode 40 after being crimped, in accordance with an embodiment of the present invention. As shown in FIGS. 4A-5B, the electrode 40 can have an elongated body that has a cross sectional shape that extends along the length of the electrode 40. The electrode 40 can be made from a malleable and conductive material such as gold, platinum, and palladium (and their respective alloys) as described previously. As will be appreciated, by forming the electrode 40 from a malleable material, the electrode 40 can be crimped or otherwise plastically deformed to transition from a first shape (i.e., FIGS. 4A and 5A) that is uncrimped to a second shape (i.e., FIGS. 4B and 5B) that is crimped. As will be described in greater detail herein, the electrode 40 can be crimped around a spine 214 to secure the electrode 40 to the spine 214 without requiring solder, weld, or adhesives.

Figure 6A:
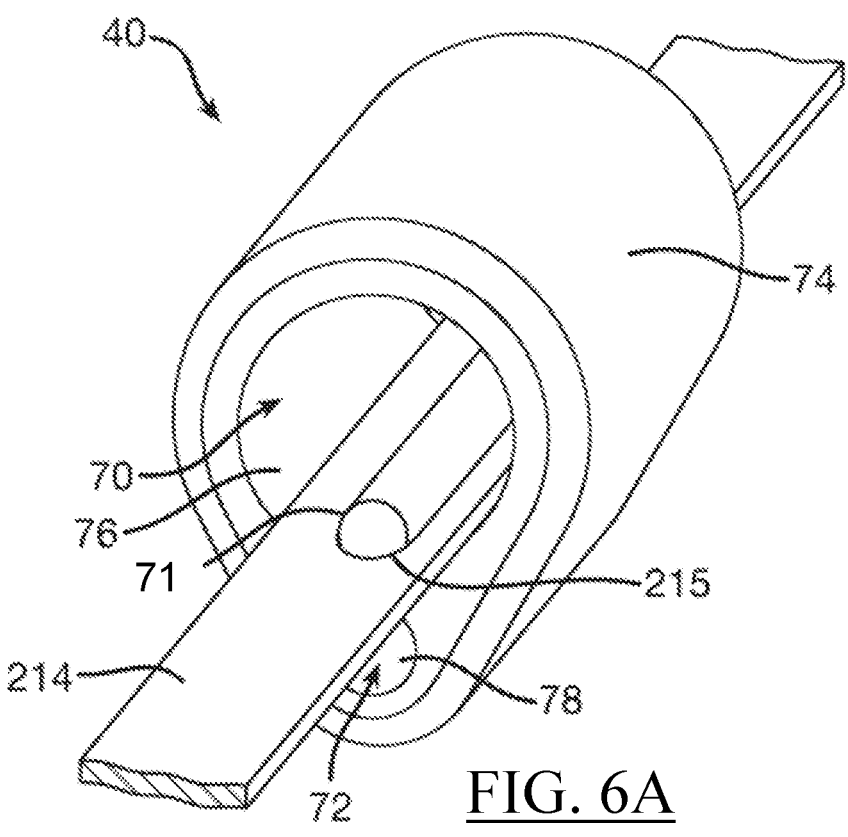

The electrode 40 can define a first lumen 70 and a second lumen 72 which both extend through an elongated body of the electrode 40 from a first end to a second end of the electrode 40. The electrode 40 can have an outer surface 74 facing outwardly from the electrode 40, a first inner surface 76 facing inwardly toward the electrode 40 where the first lumen 70 is formed through the electrode 40, and a second inner surface 78 facing inwardly toward the electrode 40 where the second lumen 72 is formed through the electrode. The first lumen 70 can be sized and configured to receive a spine 214, as shown in FIG. 6A, such that the spine 214 can pass through the first lumen 70. Although not shown, the second lumen 72 can be sized to receive a wire of the medical probe 22 such that the electrode 40 can be attached to the wire. The wire can be electrically insulated from the spine 214. In some examples, the first lumen 70 and/or the second lumen 72 can each pass through the electrode 40 in a generally longitudinal direction of the electrode 40. In other examples, the first lumen 70 and/or the second lumen 72 can pass through the electrode 40 in a generally transverse direction of the electrode 40. Furthermore, the first lumen 70 and/or the second lumen 72 can be positioned in the electrode 40 nearer a bottom surface, nearer at top surface, or nearer a middle of the electrode 40 depending on the particular configuration.

By including a first lumen 70 that is sized to receive the spine 214 of the medical probe 22, the disclosed technology can ensure the electrodes 40 are secured to the spines 214 and prevented from breaking free. Thus, even if the electrodes 40 become dislodged, the electrodes 40 will remain attached to the spines 214 by nature of the strut 430 passing through the first lumen 70.

The electrode 40 can further include a locking stub 80 that can extend inwardly into the first lumen 70. The locking stub 80 can extend longitudinally along the length of the electrode 40 from a first end of the electrode 40 to a second end of the electrode 40. The locking stub 80 can be sized to extend at least partially through an aperture 215 of the spines 214 when the electrode 40 is coupled to the spine 214.

Figure 6B:
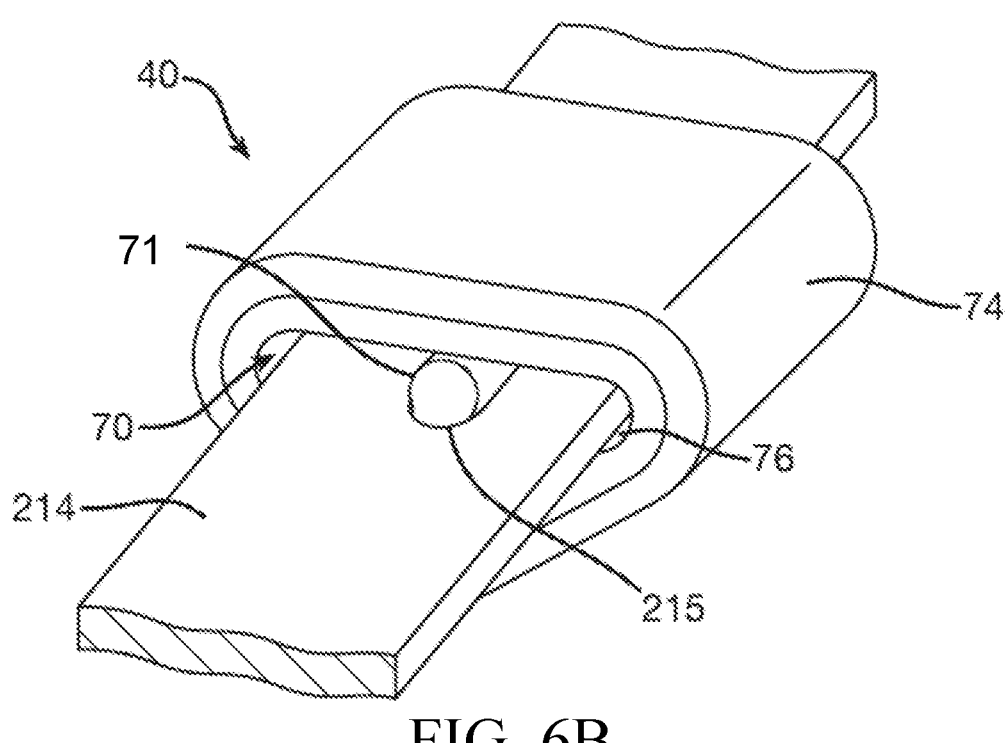
FIG. 6B is a schematic pictorial illustration showing a front perspective view of an electrode and a spine after the electrode is crimped to the spine, in accordance with an embodiment of the present invention.

As illustrated in FIGS. 4A-6B, the electrode 40 can be crimped from a first shape (i.e., as illustrated in FIGS. 4A, 5A, and 6A) to a second shape (i.e., as illustrated in FIGS. 4B, 5B, and 6B). For example, the electrodes 40 can be crimped toward a longitudinal axis of the elongated body of the electrode 40 and have a substantially rounded outer surface 74 prior to being crimped and a substantially flat outer surface 74 after being crimped. The electrodes 40 can be crimped by using a tool to press the electrode 40 until the electrode 40 plastically deforms from the first shape to the second shape. As illustrated in FIGS. 6A and 6B, a spine 214 can be inserted into the electrode 40 and an aperture 215 of the spine 214 can be aligned with the locking stub 80 of the electrode 40. Once the locking stub 80 is aligned with the aperture 215, the electrode 40 can be crimped until a distance between the locking stub 80 and the first lumen inner surface 76 is reduced and the spine 214 is secured in place. In other words, the spine 214 can be inserted into the first lumen 70 and then the electrode 40 can be crimped until electrode 40 is tightly secured around the spine 214. When the electrode 40 is crimped around the spine 214, the locking stub 80 can extend through the aperture 215 of the spine 214 and the electrode 40 can be prevented from moving proximally or distally along the length of the spine 214. Stated otherwise, once the electrode 40 is crimped to spine 40, the locking stub 80 can contact an inner surface of the aperture 215 of the spine 214 and the first lumen inner surface 76 can contact the spine 214 such that the spine 214 cannot be removed from the electrode 40 without deforming the electrode 40. In some examples, the locking stub 80 can form an interference fit with the spine 214 at the aperture 215 to secure the electrode 40 in place.

Figures 7A, 7B, 7C, 7D:
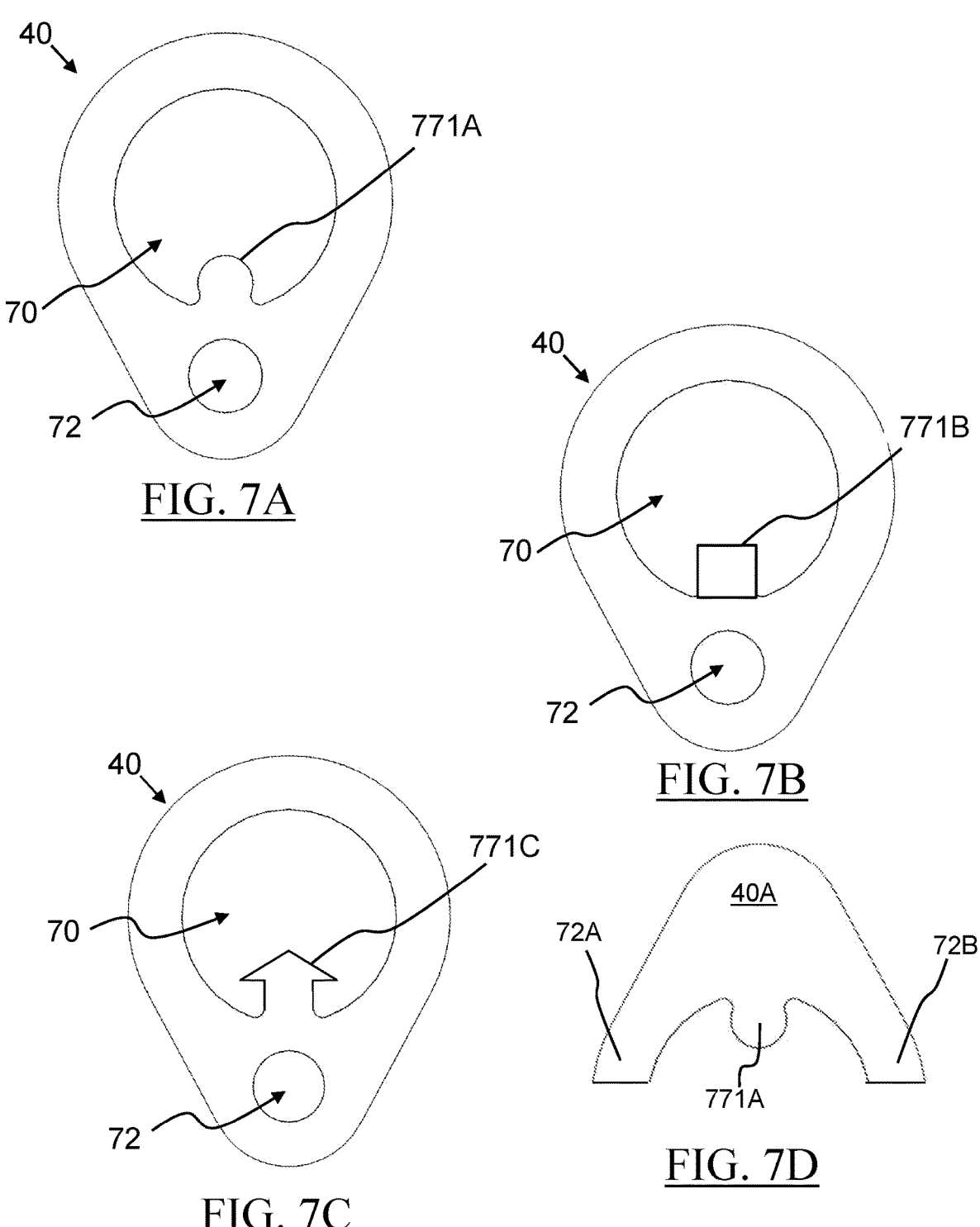
FIGS. 7A-7D illustrate side views of electrodes, in accordance with embodiments of the present invention.

FIGS. 7A-7D illustrate side views of electrodes 40 having locking stubs 780A-780C of different shapes. As shown in FIG. 7A, a locking stub 780A can comprise a generally rounded or circular cross section. Alternatively, as shown in FIG. 7B, a locking stub 780B can comprise a generally rectangular cross section or, as shown in FIG. 7C, a locking stub 780C can comprise at least a portion that has a generally triangular shape. As will be appreciated, a generally rounded locking stub 780A can help to permit the locking stub 780A to slide into the aperture 215 of the spine 214 and form an interference fit with the spine 215. Alternatively, a locking stub 780B having a generally rectangular shape may be able to form a tighter interference fit. Furthermore, a locking stub 780C having a generally triangular shape may be able to lock the spine 214 onto the locking stub 80 with the triangular shape to further secure the electrode 40 to the spine 214. In FIG. 7D, the active electrode surface 40A is now a bulging member with two side prongs 72A and 72B so that the retainer 771A can be inserted into aperture 215 and the electrode 40A is swaged or crimped over the spine member 214. In an alternative arrangement, side prongs 72A and 72B can be eliminated so that only retainer 771A project into the aperture 215 and the electrode 40A can be crimped into a substantially three-dimensional trapezoid (i.e., a rounded trapezoidal prism or rounded and truncated pyramid). As will be appreciated, FIGS. 7A-7D are offered for explanatory purposes and the disclosed technology should not limited to the specific examples of locking stubs 780A-780C illustrated and described herein. For example, the locking stub 80 can include a generally trapezoidal, pentagonal, hexagonal, octagonal, elliptical, cross, curved, or other suitable shape. Furthermore, the locking stub 80 can have a changing cross section along the length of the locking stub 80 from one end of the locking stub 80 to another end of the locking stub 80. For example, the locking stub 80 can have a thicker cross section at either end of the locking stub 80 or a thicker cross section at the middle of the locking stub 80. Furthermore, although described as extending from one side of the electrode 40 to a second side of the electrode 40, the locking stub 80 can extend less than the full length of the electrode 40 or may have a portion removed between the first end and second end (e.g., the locking stub 80 can have portions of material at either end of the electrode 40 with no material at the middle of the electrode 40). Further still, although a single locking stub 80 is shown and described herein, the electrode 40 can include more than one locking stub 80 and the locking stub 80 can extend into the first lumen 70 from a portion of the first lumen 70 other than the lower portion of the lumen 70 (e.g., an upper portion of the lumen 70). Accordingly, the disclosed technology should not be construed as limited to the particular configurations shown and described herein.

Returning now to FIGS. 5A and 5B, the electrode 40 can include a conductive portion 90 and an insulative portion 92. The conductive portion 90 can be configured to permit electricity to pass therethrough (i.e., for ablation or mapping of the cardiac tissue) and can face generally outward from the basket assembly 80 to face cardiac tissue when in use. The insulative portion 92, on the other hand, can be configured to prevent electricity from passing therethrough to help electrically isolate the spine 214 from the electrode 40. In this way, the insulative portion 92 can prevent a short circuit from forming between the electrode 40 and the spine 214. Alternatively, or in addition, the spine 214 can be made from an insulative material or have an insulative coating or sleeve added thereto to electrically isolate the electrode 40 from the spine 214. As yet another example, an electrically insulating material can be placed between the electrode 40 and the spine 214 to electrically isolate the electrode 40 from the spine 214.

Embodiments of the present invention may include a spine member (e.g., spine 214 of FIGS. 8A-8C) for an end effector the spine member extending along a longitudinal axis 213 from a proximal end 216 to a distal end 217. The spine member 214 includes a unidirectional proximal stop member (e.g., proximal stop 220 of FIGS. 8A-8C) to allow an electrode (e.g. distal electrode 40B of FIG. 8C) to slide in a direction distally but not proximally and a distal stop member (e.g., distal stop 222 FIGS. 8A-8C) to prevent an electrode (e.g., distal electrode 40B) from sliding past.

Embodiments of the present invention may include an expandable basket assembly 38 for a medical probe 22. The expandable basket assembly 38 may include a plurality of spines 214 configured to bow radially outward from a central axis 86 when the expandable basket assembly 38 is transitioned from a collapsed form to an expanded form. Each spine 214 of the plurality of spines 214 may include a proximal electrode stop (e.g., proximal electrode stop 220 of FIG. 8A) configured to allow a distal electrode (e.g., distal electrode 40B of FIG. 8C) to slide distally on each spine 214 past the proximal electrode stop (e.g., proximal electrode stop 220 of FIGS. 8A-8C) but prevent a proximal electrode (e.g., proximal electrode 40A of FIG. 8C) from sliding distally past the proximal electrode stop (e.g., proximal electrode stop 220 of FIG. 8A). Each spine 214 may also include a distal electrode stop (e.g., distal electrode stop 222 of FIGS. 8A-8C) configured to prevent the distal electrode (e.g., distal electrode 40B of FIG. 8C) from sliding distally past the distal electrode stop (e.g., distal electrode stop 222 of FIGS. 8A-8C).

Figures 8A, 8B:
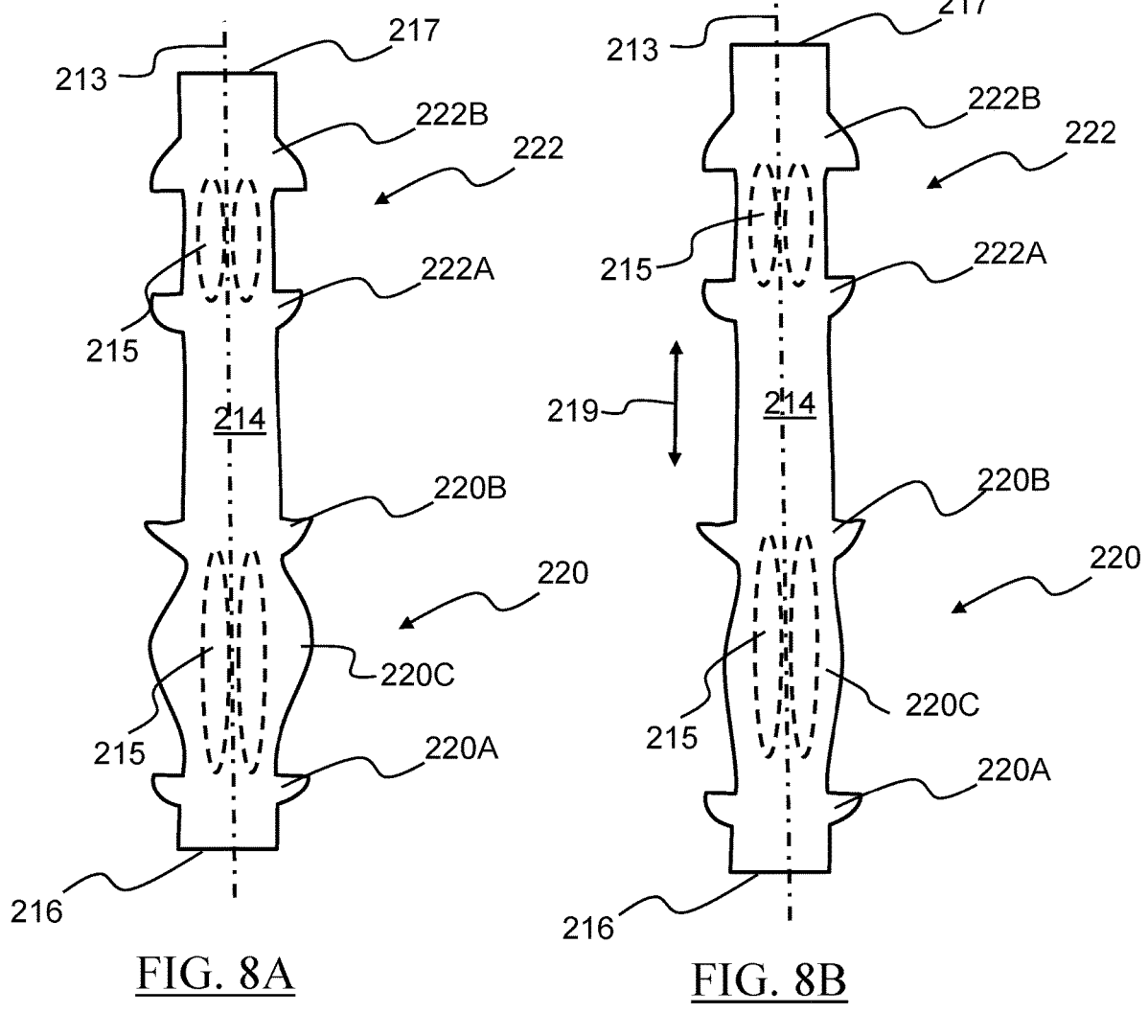
FIG. 8A is a top view of a bulged spine in a default state, in accordance with embodiments of the present invention.
FIG. 8B is a top view of the spine of FIG. 8A in a stretched state, in accordance with embodiments of the present invention.
Figure 8C:
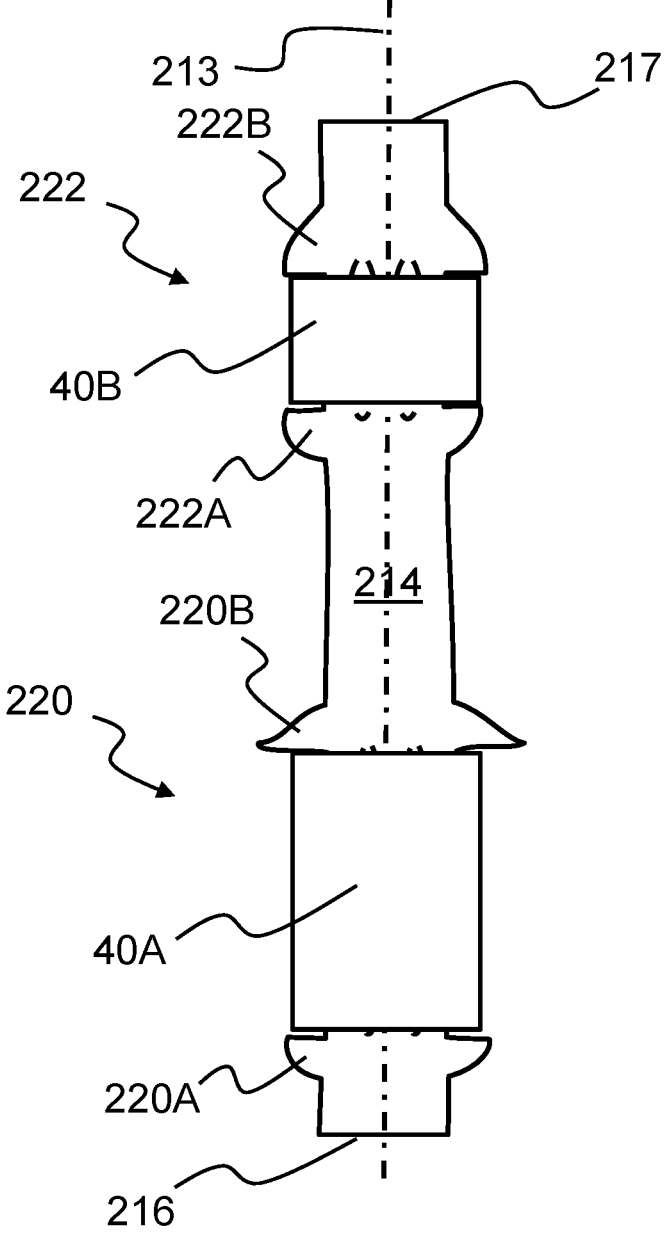
FIG. 8C is a top view of the spine of FIG. 8A with electrodes, in accordance with embodiments of the present invention.

FIGS. 8A-8C are top views of one or more embodiments of a spine 214 for an expandable basket assembly 38 with a proximal electrode stop 220 and a distal electrode stop 222. The proximal electrode stop 220 may include a bulged portion 220C configured to prevent to retain an electrode in place when the spine 214 is in a default unstretched state (e.g., in a longitudinal direction 219). However, when the spine 214 is stretched (e.g., in a longitudinal direction 219), the bulged portion 220C stretches out to reduce its maximum width, allowing a distal electrode 40B to pass over it as well as allows for a proximal 40A to be installed over it. The spine 214 may also include a pair of first proximal protrusions 220A extending from opposing sides of the spine 214 with first proximal facing portions angled away from a proximal end 216 of the spine 214 and first distal facing portions approximately parallel with the proximal end 216 of the spine 214 such that the first distal facing portions are configured to further prevent the proximal electrode 40A from sliding proximally. The spine 214 may also include a pair of second proximal protrusions 220B extending from the opposing sides of the spine 214.

The second proximal protrusions 220B may have second proximal facing portions angled away from the proximal end 216 of the spine 214 such that the pair of second proximal protrusions 220B are configured to allow a distal electrode 40B to slide distally on the spine 214 past the pair of second proximal protrusions 220B but prevent a proximal electrode 40A from sliding distally the pair of second proximal protrusions 220B. Moreover, the second proximal protrusions 220B may slope further away from the proximal end 216 of the spine 214 when the spine 214 is stretched in the longitudinal direction 219 further contributing to allowing a distal electrode 40B to slide over and into position distal to the proximal electrode stop 220. The pair of second proximal protrusions 220B may also have second distal facing portions also angled away from the proximal end 216 of the spine 214 or approximately parallel with the proximal end 216 of the spine 214.

The spine 214 may also include pairs of first and second distal protrusions 222A, 222B extending from opposing sides of the spine 214. The pair of first distal protrusions 222A may include distal facing portions that are approximately parallel with a proximal end 216 of the spine 214 such that it is configured to prevent a distal electrode 40B from sliding proximally. The pair of second distal protrusions 222B may include proximal facing portions that are approximately parallel with a proximal end 216 of the spine 214 such that it is configured to prevent the distal electrode 40B from sliding distally.

The spine 214 may include one or more apertures 215 extending through from a first side of the spine 214 to a second side of the spine 214. The one or more apertures 215 may be configured to receive a locking stub 80 of the proximal or distal electrode such that when the proximal and/or distal electrode 40A, 40B is mechanically coupled to the spine, the locking stub 80 extends through the aperture further preventing the proximal and/or distal electrode 40A, 40B from sliding distally or proximally along the spine 214.

Figures 9A, 9B:
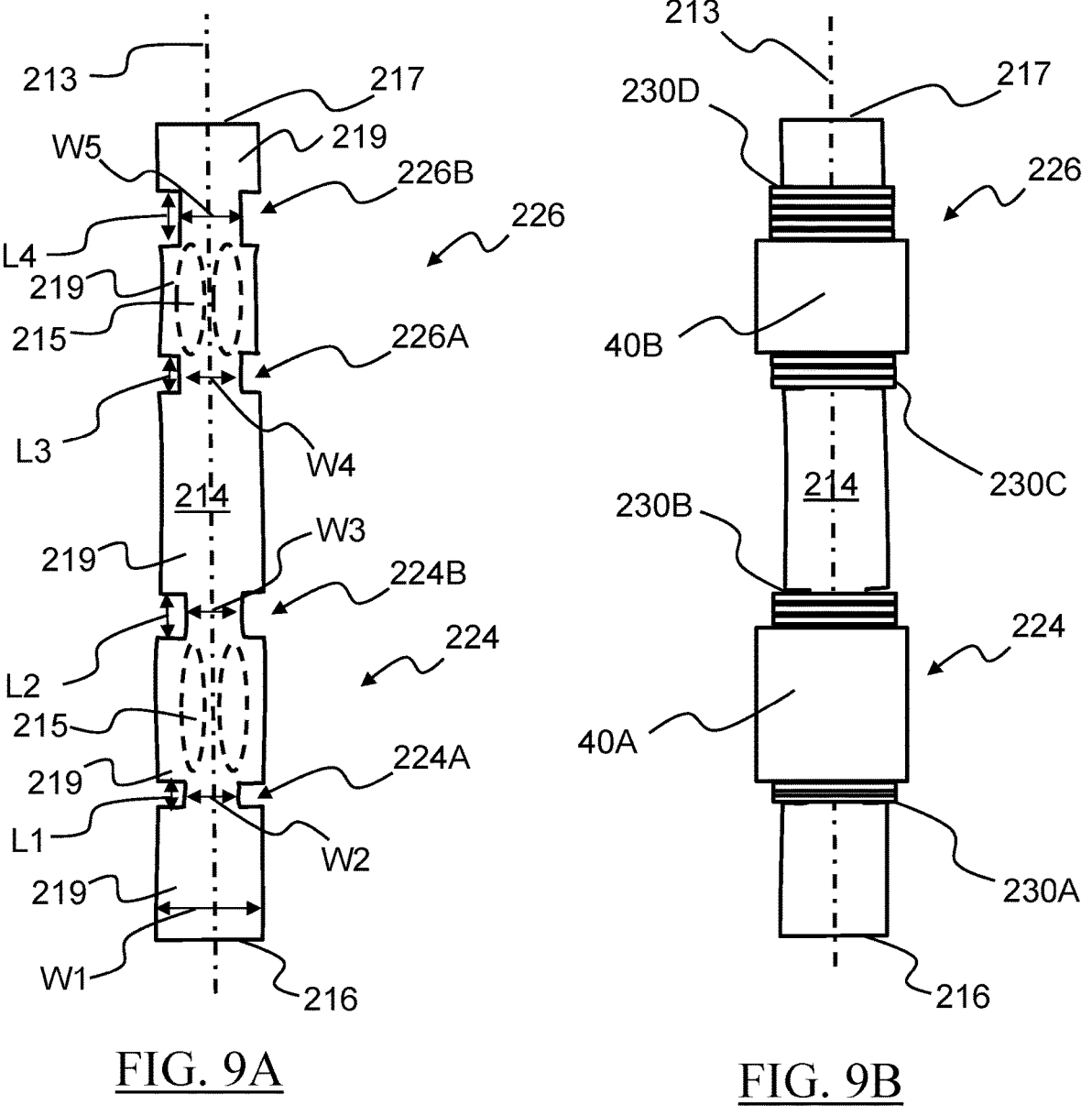
FIG. 9A is a top view of a spine with one or more lateral cutouts, in accordance with embodiments of the present invention.
FIG. 9B is a top view of the spine of FIG. 9A with one or more coils and electrodes, in accordance with embodiments of the present invention.

FIGS. 9A and 9B are top views of one or more embodiments of a spine 214 for an expandable basket assembly 38 that may include a proximal electrode stop 224 that may include a first pair of lateral cut outs 224A and a second pair of lateral cutouts 224B. The first and second pairs of lateral cutouts 224A. 224B may be configured to receive first and second coils 230A, 230B which, when installed, may be configured to prevent a proximal electrode 40A from moving distally or proximally. In contrast, before the coils 230A, 230B are installed, a distal electrode 40B may be slid from the proximal end 216, past the proximal electrode stop 224, to the distal electrode stop 226. The distal electrode stop 226 may also include first and second pairs of lateral cutouts 226A, 226B configured to respectively receive coils 230C and 230D, which, when installed, may be configured to prevent a distal electrode 40B from moving distally or proximally. The spine 214 may also include one or more apertures 215 as described above.

Put another way, as shown in FIG. 9A, the spine 214 may have a first width W1 at a plurality of spine portions 219, a second width W2 for a first length L1, a third width W3 for a second length L2, a fourth width W4 for a third length L3, and a fifth width W5 for fourth length L4. In some embodiments, widths W2, W3, W4, and W5 may be the same or different. Similarly lengths L1, L2, L3, and L4 may be the same or different. The various width W1, W2, W3, W4, and W5 and lengths L1, L2, L3, and L4 of spine 214 correspond to and form pairs of lateral cutouts 224A, 224B, 226A, 226B described above.

Figures 10A, 10B:
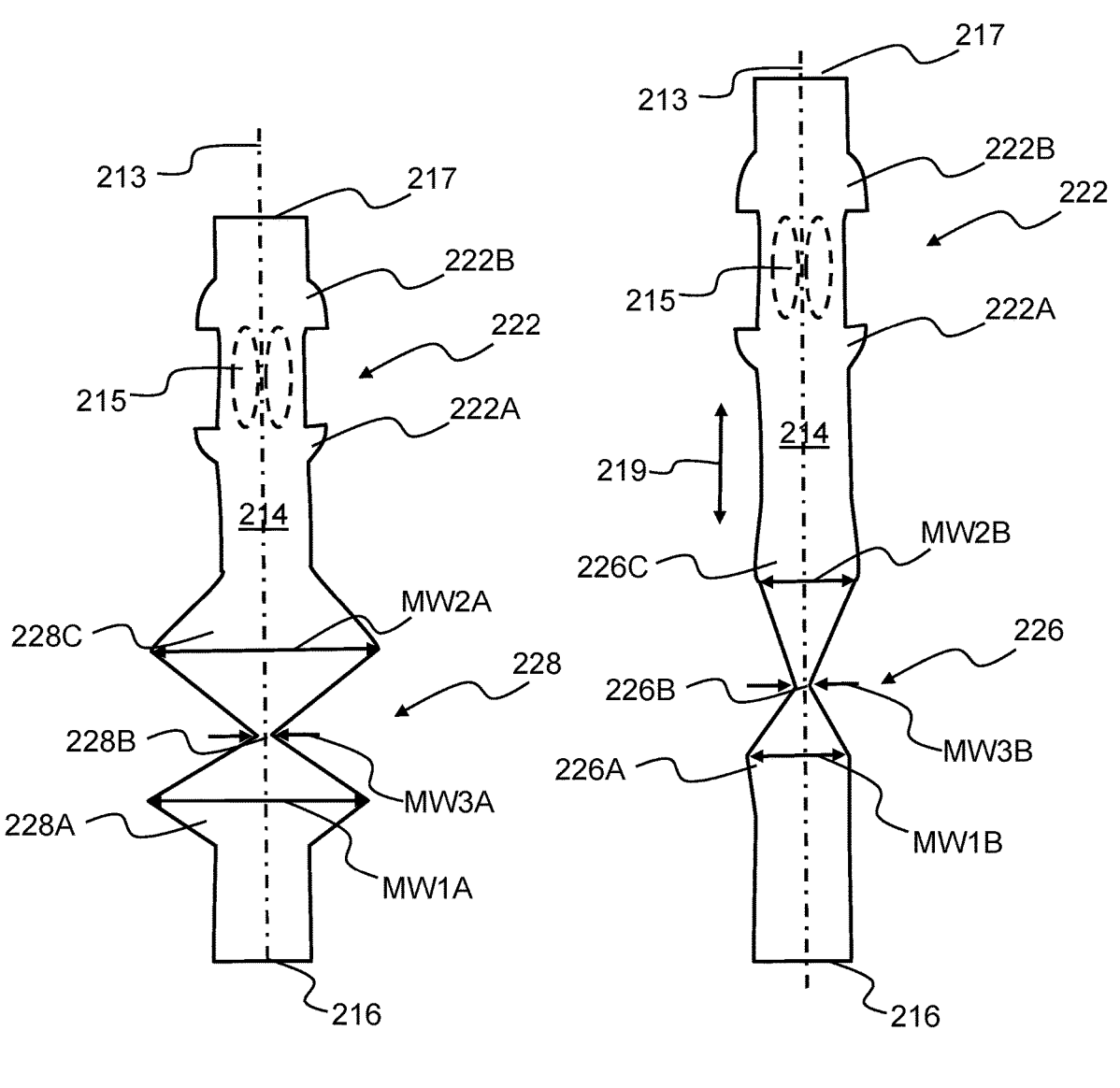
FIG. 10A is a top view of a spine with an electrode stop having with a proximal and distal diamond portions in a default state, in accordance with embodiments of the present invention.
FIG. 10B is a top view of the spine of FIG. 10A in a stretch state, in accordance with embodiments of the present invention.
Figure 10C:
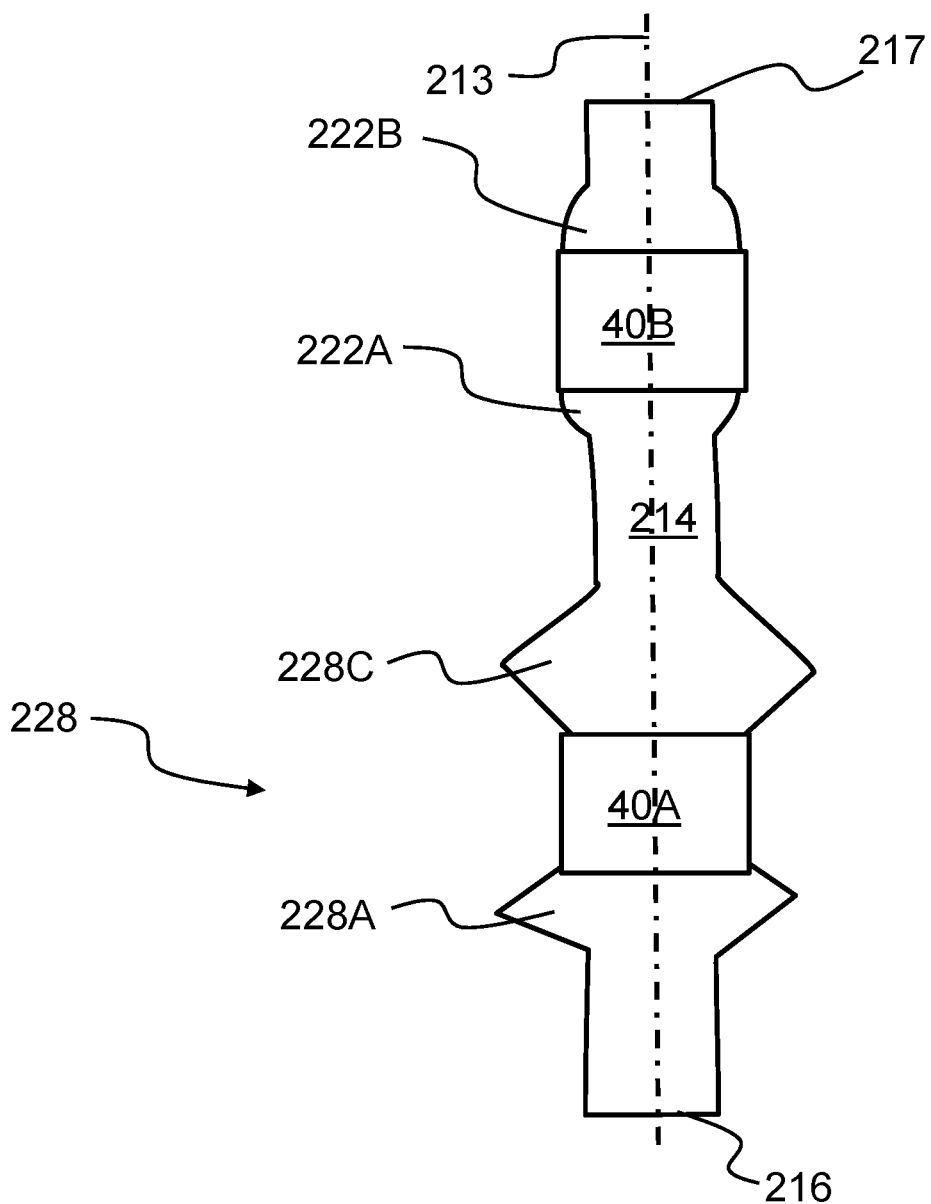
FIG. 10C is a top view of the spine of FIG. 10A with electrodes, in accordance with embodiments of the present invention.

FIGS. 10A-10C are similar to FIGS. 8A-8C, except spine 214 of FIGS. 10A-10C may use one or more diamond portions 228A, 228B, 228C instead of a middle bulge for a proximal electrode stop 228. In particular, the proximal electrode stop 228 may include a proximal diamond portion 228A, a distal diamond portion 228C, and a diamond intersection 228B connected to the proximal and distal diamond portions 228A, 228C. In a default unstretched state shown in FIGS. 10A and 10C, the proximal diamond portion 228A is configured to prevent the proximal electrode 40A from sliding proximally by having a first proximal maximum width MW1A that is equal to or greater than a diameter of a lumen of the proximal electrode 40A. Similarly, the distal diamond portion 228C is configured to prevent the proximal electrode 40A from sliding distally in the default state by having a first distal maximum width MW2A that is equal to or greater than a lumen of the proximal electrode 40A. In an expanded state (e.g., stretched in the longitudinal direction 219) shown in FIGS. 10B, the proximal diamond portion 228A and the distal diamond portion 228C are configured to allow the distal electrode 40B to slide over them distally by changing to respectively have second proximal and second distal maximum widths MW1B, MW2B that are less than a diameter of a lumen of the distal electrode 40B. Diamond intersection 228B may have a second maximum width MW3B that is less than a diameter of a lumen of the proximal and distal electrodes 40A and 40B when the spine is in the expanded state and may have a first maximum width MW3A that is less or equal to a diameter of a lumen of the proximal and distal electrodes 40A and 40B. In some embodiments, spine 214 may not include the proximal diamond portion 228A and may instead have a pair of protrusions 220A as shown in FIG. 8A.

FIGS. 11A and 11B are similar to FIGS. 8A-8C, except proximal electrode stop 220 of FIGS. 11A and 11B includes a distal aperture 221 in place of second proximal protrusions 220B and a bulge 220C. The distal aperture 221 may be configured to receive a protrusion 231A of a retainer rivet 231. The retainer rivet may include a non-conducting material such a polymer. The retainer rivet 231 can retain the electrode 40A and prevent both proximal and distal movement. The retainer rivet 231 can protrude just through the spine 214 and act as a barrier or can also extend through a rivet aperture on the electrode 40A and act as a nail, fixing the electrode 40A to the spine 214.

Figures 12A, 12B:
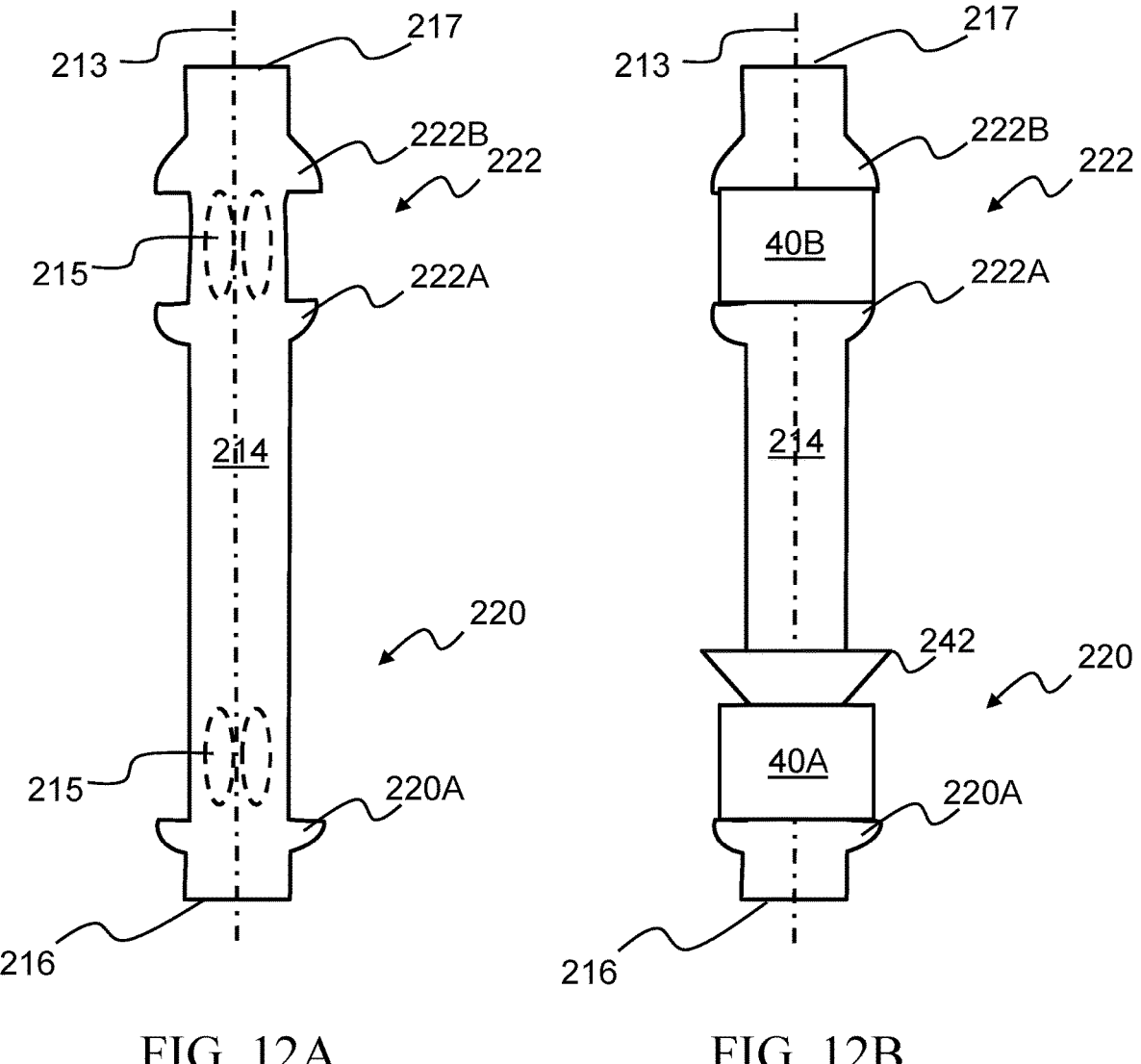
FIG. 12A is a top view of a spine with an electrode stop having proximal protrusions, in accordance with embodiments of the present invention.
FIG. 12B is a top view of the spine of FIG. 12A with electrodes and a shim configured to retain a proximal electrode, in accordance with embodiments of the present invention.

FIGS. 12A and 12B are similar to FIGS. 11A and 11B, but may omit the distal aperture 221. Instead, a shim 242 may be slid past the proximal electrode stop 220 after the distal electrode 40B is slid to the distal electrode stop 222. Then, the shim 242 may be inserted into a lumen of the proximal electrode 40A to prevent distal movement of the proximal electrode 40A. In some embodiments, the shape of the shim 242 may gradually increase in width from a proximal end to a distal end thereof.

Figures 13A, 13B:
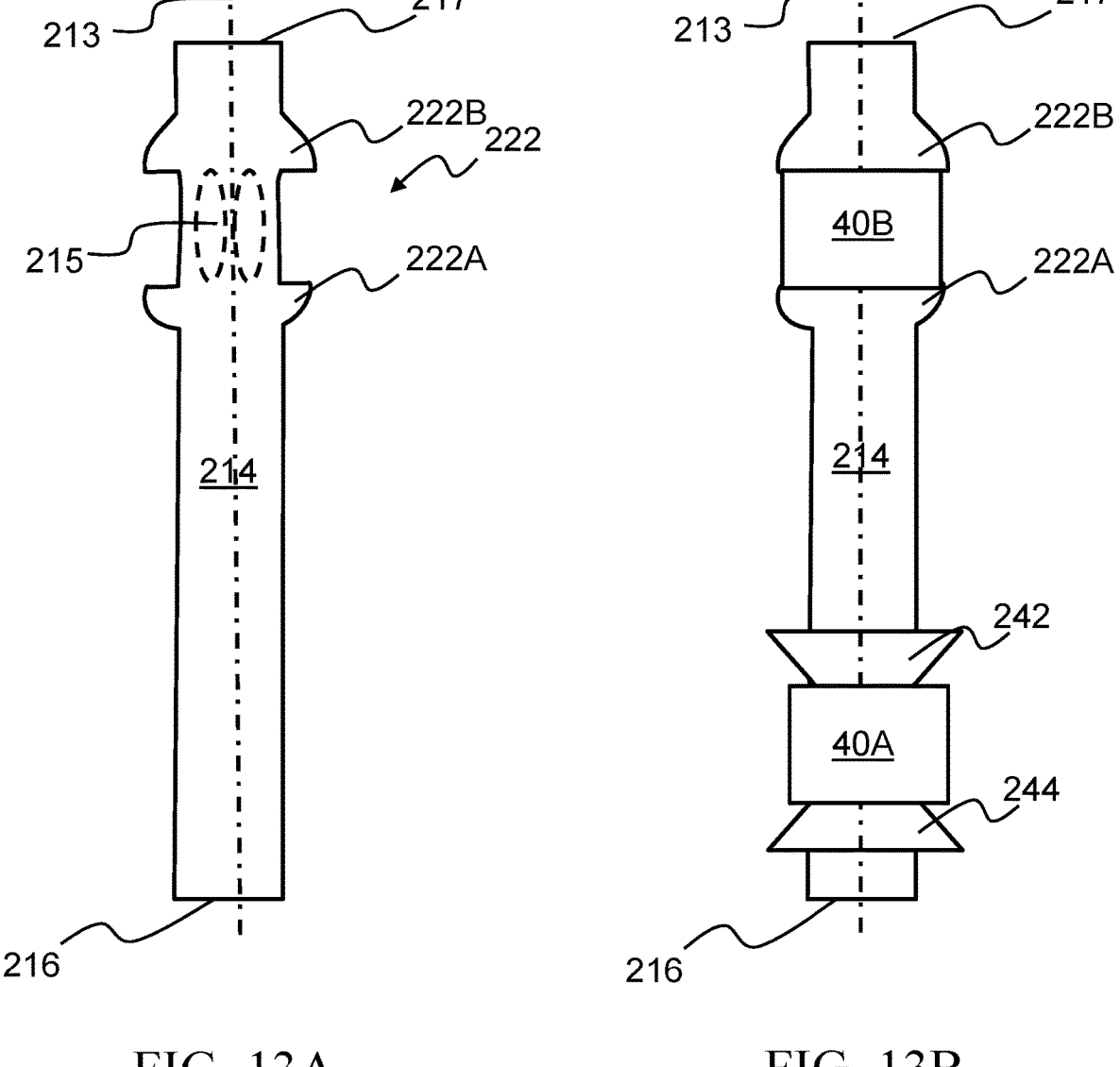
FIG. 13A is a top view of a spine without protrusions for a proximal electrode stop, in accordance with embodiments of the present invention.
FIG. 13B is a top view of the spine of FIG. 13A with electrodes and proximal and distal shims configured to retain a proximate electrode from sliding, in accordance with embodiments of the present invention.

FIGS. 13A and 13B are similar to FIGS. 12A and 12B, but may omit first proximal protrusions 220A. Instead, a second shim 244 may be inserted into a lumen at a proximal end of the proximal electrode 40a to prevent proximal movement of the proximal electrode 40A. In some embodiments, the shape of the shim 244 may gradually decrease in width from a proximal end to a distal end thereof.

Figures 14A, 14B:
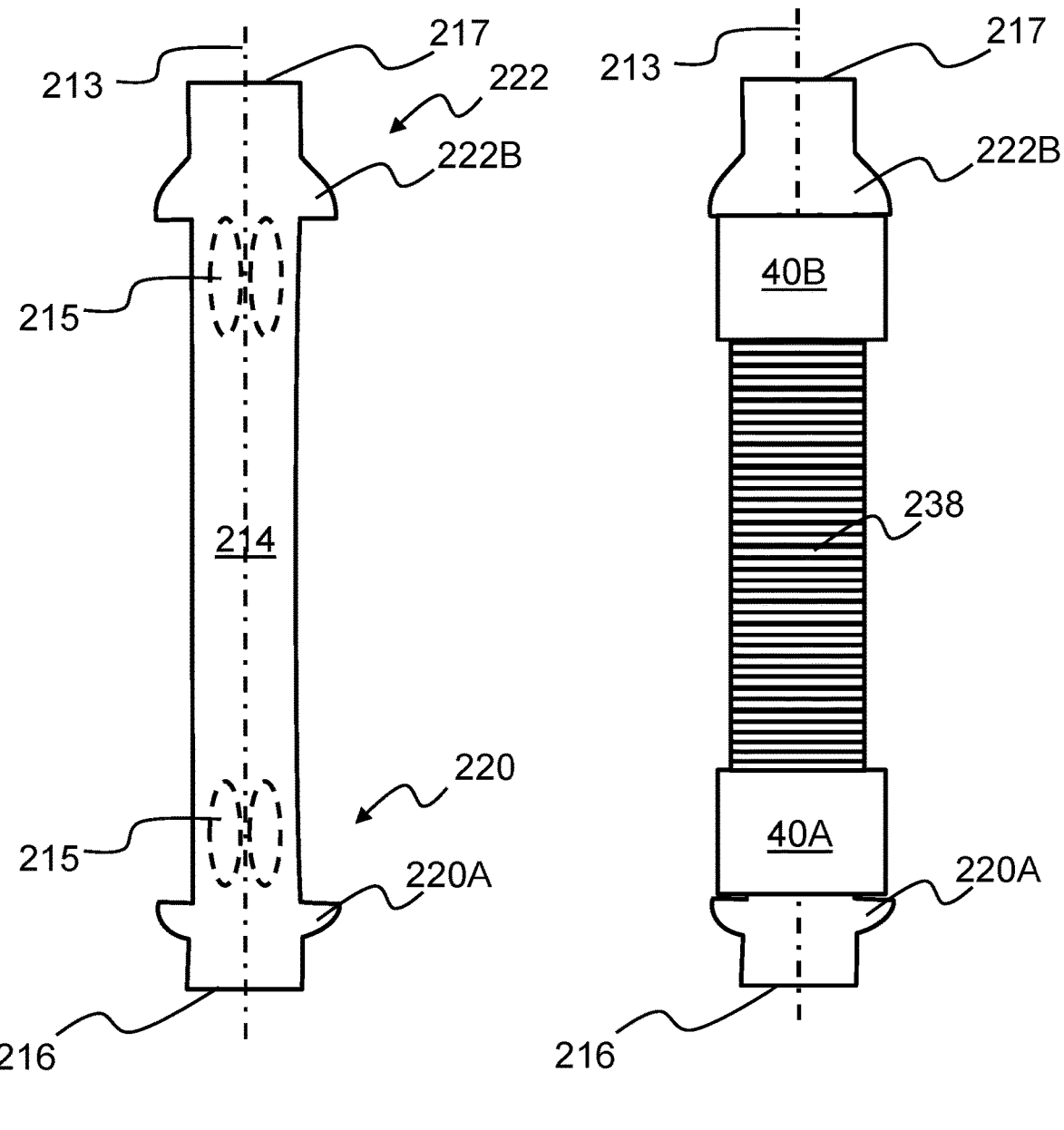
FIG. 14A is a top view of a spine without distal protrusions for a proximal electrode stop and without proximal protrusions for a distal electrode stop, in accordance with embodiments of the present invention.
FIG. 14B is a top view of the spine of FIG. 14A with electrodes and a flexible member disposed between the electrodes, in accordance with embodiments of the present invention.

FIGS. 14A and 14B are similar to FIGS. 12A and 12B, except that the spine 214 of FIGS. 14A and 14B does not include a pair of first distal protrusions 222A or a shim 242. Instead, after a distal electrode 40B is slid adjacent to a pair of second distal protrusions 222B, a flexible member 238 (e.g., a spring) may be placed proximal the distal electrode 40B. Finally, a proximal electrode is placed proximal the flexible member 238 and distal the pair of first proximal protrusions 220A. The flexible member 238 may be configured to prevent proximal movement of the distal electrode 40B and distal movement of the proximal electrode 40A and may hold, with a spring force, the proximal electrode 40A against the pair of first proximal protrusions 220A and the distal electrode 40B against the pair of second distal protrusions 222B.

Figures 15A, 15B, 15C, 15D:
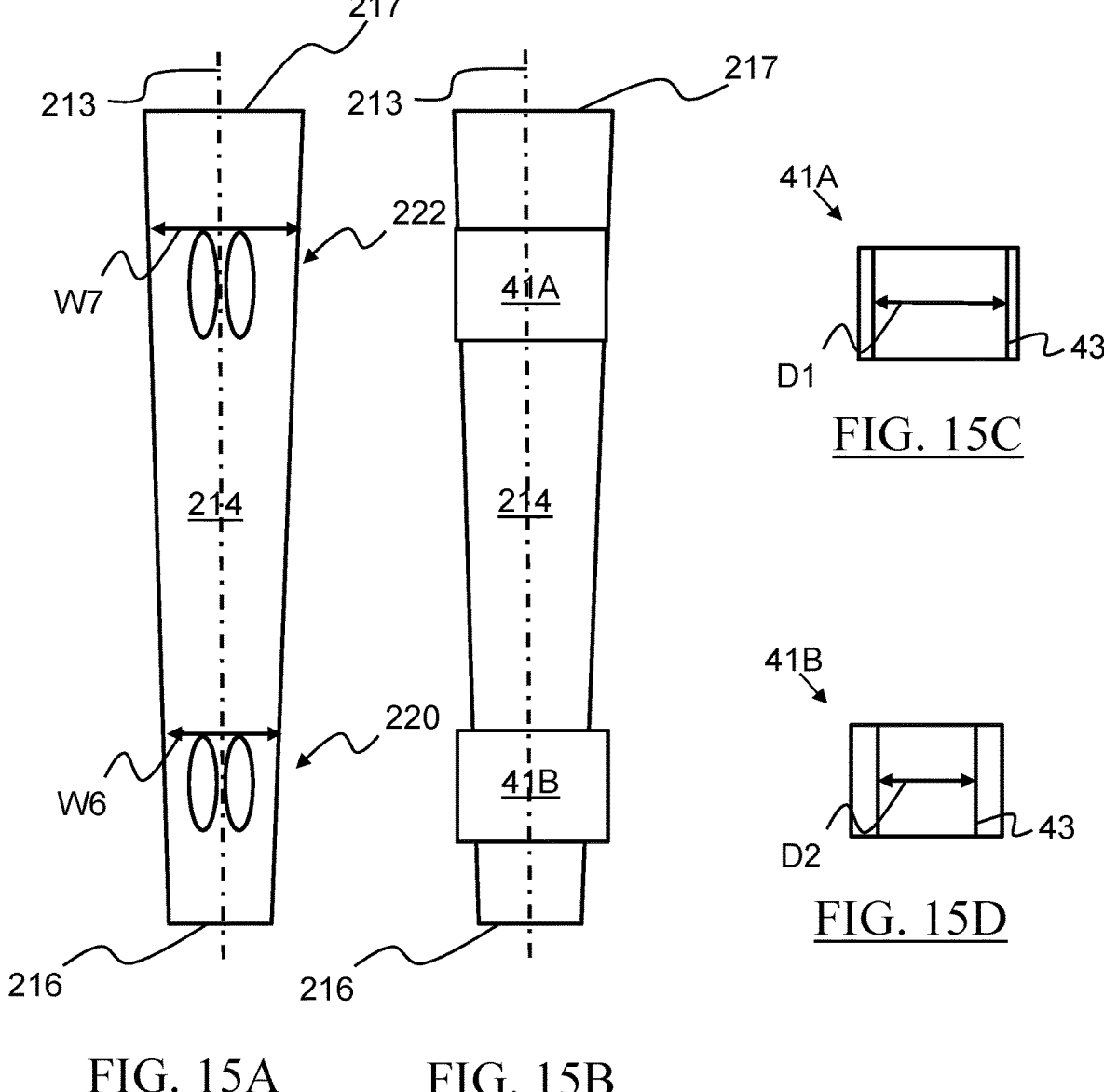
FIG. 15A is a top view of a spine with a width that changes from proximal portion to a distal portion of the spine, in accordance with embodiments of the present invention.
FIG. 15B is a top view of the spine of FIG. 15A with electrodes, in accordance with embodiments of the present invention.
FIG. 15C is a cut away top view of a distal electrode with a lumen having a first diameter, in accordance with embodiments of the present invention.
FIG. 15D is a cut away top view of a proximal electrode with a lumen having a second diameter, in accordance with embodiments of the present invention.

FIGS. 15A and 15B are top views of a spine 214, with a proximal end 216, that has a sixth width W6 of a distal portion of the proximal electrode stop 220 and a second width W7 of a distal portion of the distal electrode stop 222. The second width W7 may be greater than the sixth width W6. FIG. 15C illustrates a cutaway top view of a distal electrode 41A that has a lumen 43 with a first diameter D1. FIG. 15D illustrates a cutaway top view of a proximal electrode 41B that has a lumen 43 with a second diameter D2. The second diameter D2 of the proximal electrode 41B may be less than the first diameter D1 and less than or equal to the sixth width W6 such that the proximal electrode 41B cannot move distally past the distal portion of the proximal electrode stop 220. The first diameter D1 of the distal electrode 41A may be less than or equal to the second width W7 such that the distal electrode 41A cannot move distally past the distal portion of the distal electrode stop 222. In some embodiments, spine 214 may have a width that gradually changes from a proximal end to a distal end and/or from the sixth width W6 to the seventh width W7.

Figures 16A, 16B, 16C:
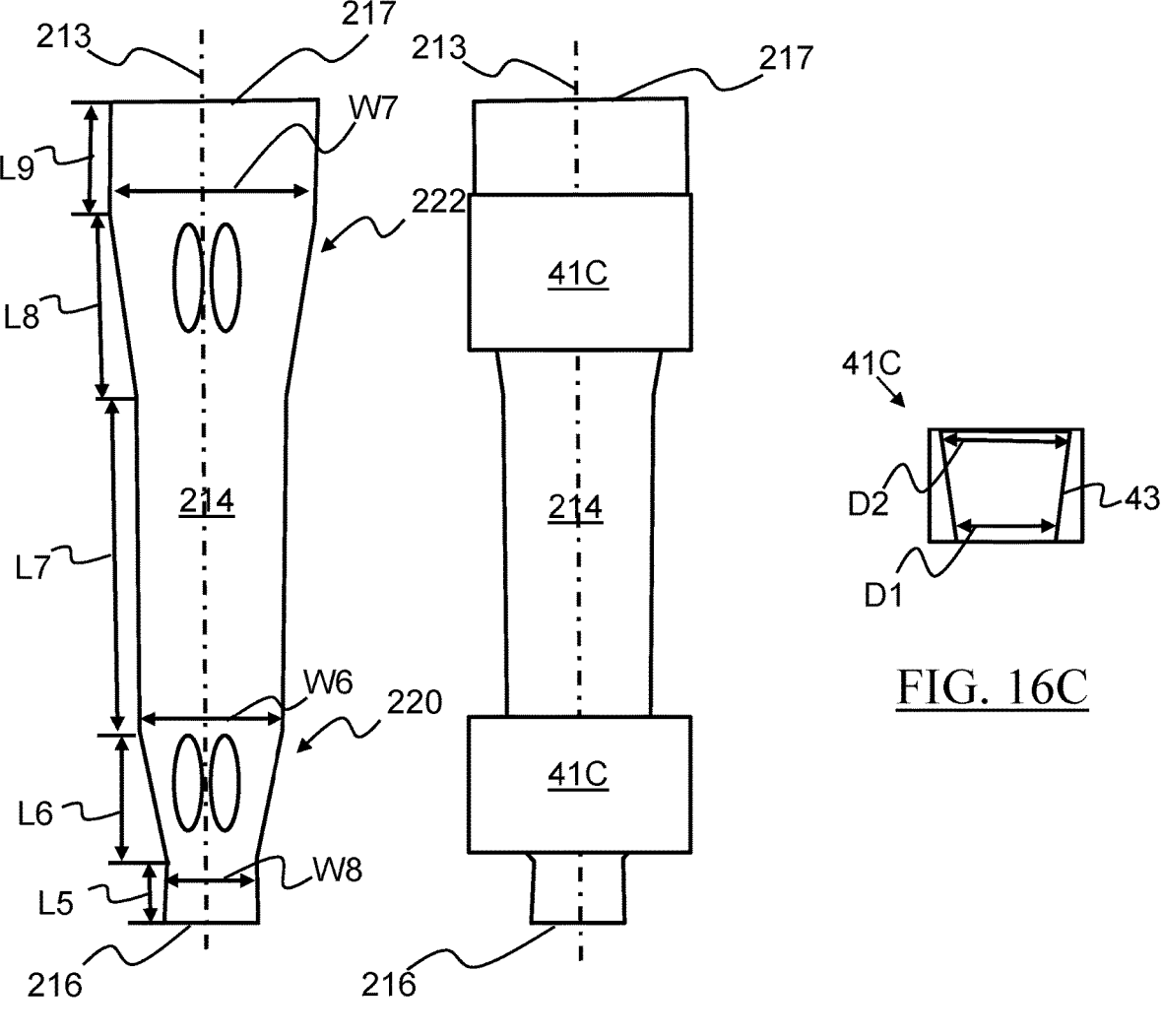
FIG. 16A is a top view of a spine with a width that changes gradually at a proximal electrode stop and a distal electrode stop, in accordance with embodiments of the present invention.
FIG. 16B is top view of the spine of FIG. 16A with electrodes, in accordance with embodiments of the present invention.
FIG. 16C is a cut away top view of an electrode configured to be installed distally or proximally depending on orientation, in accordance with embodiments of the present invention.

FIGS. 16A and 16B are top views of spine 214, according to one or more embodiments, similar to FIGS. 15A and 15B, except that the spine 214 of FIGS. 16A and 16B have gradually increasing widths at the proximal and distal electrode stops 220, 222, but not in other portions of the spine 214. Such a shape allows spine 214 of FIGS. 16A and 16B to receive the same electrode 41C (see FIG. 16C), but differently orientated depending on desired position at the distal or proximal electrode stops 222, 220. In some embodiments, spine 214 of FIGS. 16A and 16B include an eighth width W8 at the proximal end 216 of spine 216 for a fifth length L5 extending away from the proximal end 216. Spine 214 may also include a second width W6 for a second length L7 with the first width W6 being greater than the eighth width W8. Spine 214 may also include the seventh width W7 for a ninth length L9 with the seventh width W7 being greater than the sixth width W6. Additionally, the eighth width W8 may gradually increase to the sixth width W6 over a sixth length L6 at the proximal electrode stop 220. The sixth width W6 may gradually increase to the seventh width W7 over an eighth length L8 at the distal electrode stop 222.

As shown in FIG. 16C, electrode 41C may include a lumen 43 that gradually changes in diameter from a first diameter D1 at a first end to a second diameter D2 at a second end with the second diameter D2 being greater than the first diameter D1. The second diameter D2 may be less than or equal to the seventh width W7 in order to prevent the electrode 41C from traveling distally past the distal electrode stop 222, especially when electrode 41C is a distal electrode orientated with the second diameter D2 being distal to the first diameter D1. Similarly, the first diameter D1 may be less than or equal to the sixth width W6 in order to prevent to the electrode 41C from traveling distally past the distal electrode stop 222.

FIGS. 17A and 17B illustrate a spine 214 similar to spine 214 of FIGS. 8A-8C, except FIGS. 17A and 17B illustrate a first electrode stop 223 with a pair of first proximal arms 223A in place of first proximal protrusions 220A and bulge 220C. The description above of the second proximal protrusions 220B of FIGS. 8A-8C applies to the second proximal protrusions 221B as these portions may be the same. The pair of first proximal arms 223A extending from opposing sides of spine 214 angled away from the proximal end of the spine 214. The pair of arms 223A are configured to close such that the distal electrode 40B can slide over the pair of arms 223A while also forming a pocket retaining the proximal electrode 40A when the proximal electrode moves proximally.

Figures 18A, 18B, 18C:
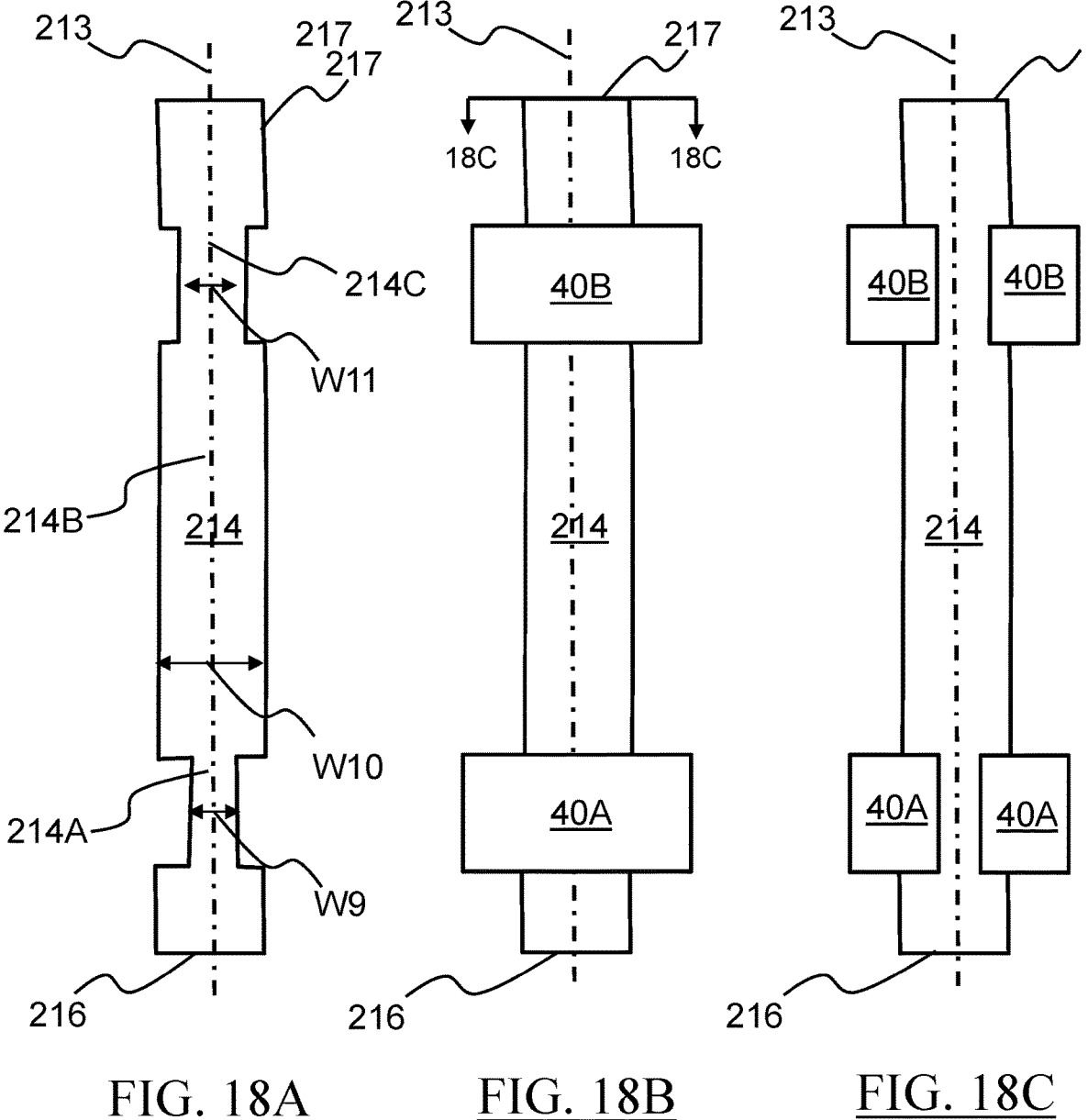
FIG. 18A is a top view of a spine with portions of reduced widths to serve as electrode stops, in accordance with embodiments of the present invention.
FIG. 18B is a top view of the spine of FIG. 18A with electrodes, in accordance with embodiments of the present invention.
FIG. 18C is a cut away top view of FIG. 18B, in accordance with embodiments of the present invention.

FIGS. 18A-18C illustrate a spine 214 with a first portion 214A configured to receive and connect with the proximal electrode 40A and having a ninth width W9. The spine 214 may include a second portion 214B having a second width W10 and a third portion 214C having a third width W11 configured to receive and connect with the distal electrode 40B. The second width W10 may be greater than the first and second third width W9, W11. FIG. 18C is a cross section top view as if the spine 214 and electrodes 40A, 40B were sliced longitudinally distally from proximal end 216.

Figure 19A:
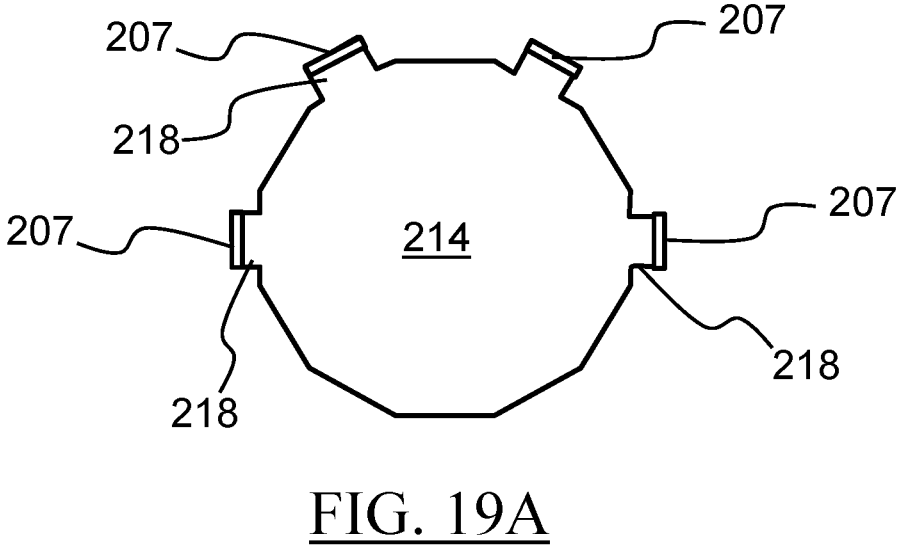
FIG. 19A a side view of a spine with electrode extensions extending radially from the spine, in accordance with embodiments of the present invention.
Figure 19B:
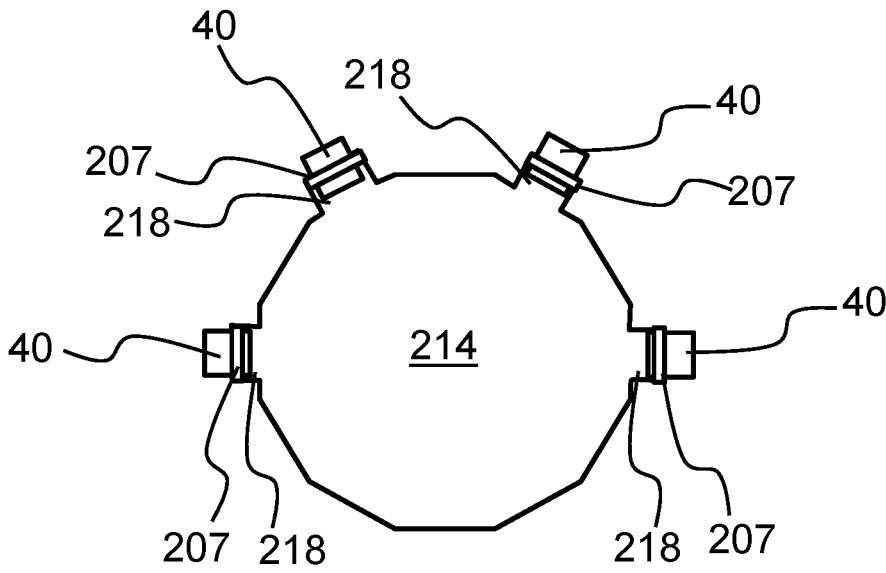
FIG. 19B is a side view of the spine of FIG. 19A with electrodes, in accordance with embodiments of the present invention.

FIGS. 19A and 19B illustrate a side cross-sectional view of a spine 214 according to one or more embodiments. The spine 214 may have a generally circular, near circular cross-section (e.g., hexagon, octagon, pentagon, dodecagon, etc.), or approximately square. Multiple electrodes can be present on one "side" of the shape, or the spine can have a shape with sides that match the number of electrodes. The spine 214 may include at least one (or a plurality of) electrode extensions 218 extending radially from the spine 214. Each electrode extension 218 may include a band 207, proximate a distal radial end thereof, configured receive and retain an electrode 40 of the plurality of electrodes 40. With such a configuration, many smaller electrodes 40 may be use making it more economical to include more expensive and rare conducting materials (e.g., platinum) as electrode materials. The bands 207 and/or the electrode extensions 218 may have adjustable heights and/or allow for the electrode 40 disposed therein to adjust radially.

Figure 20:
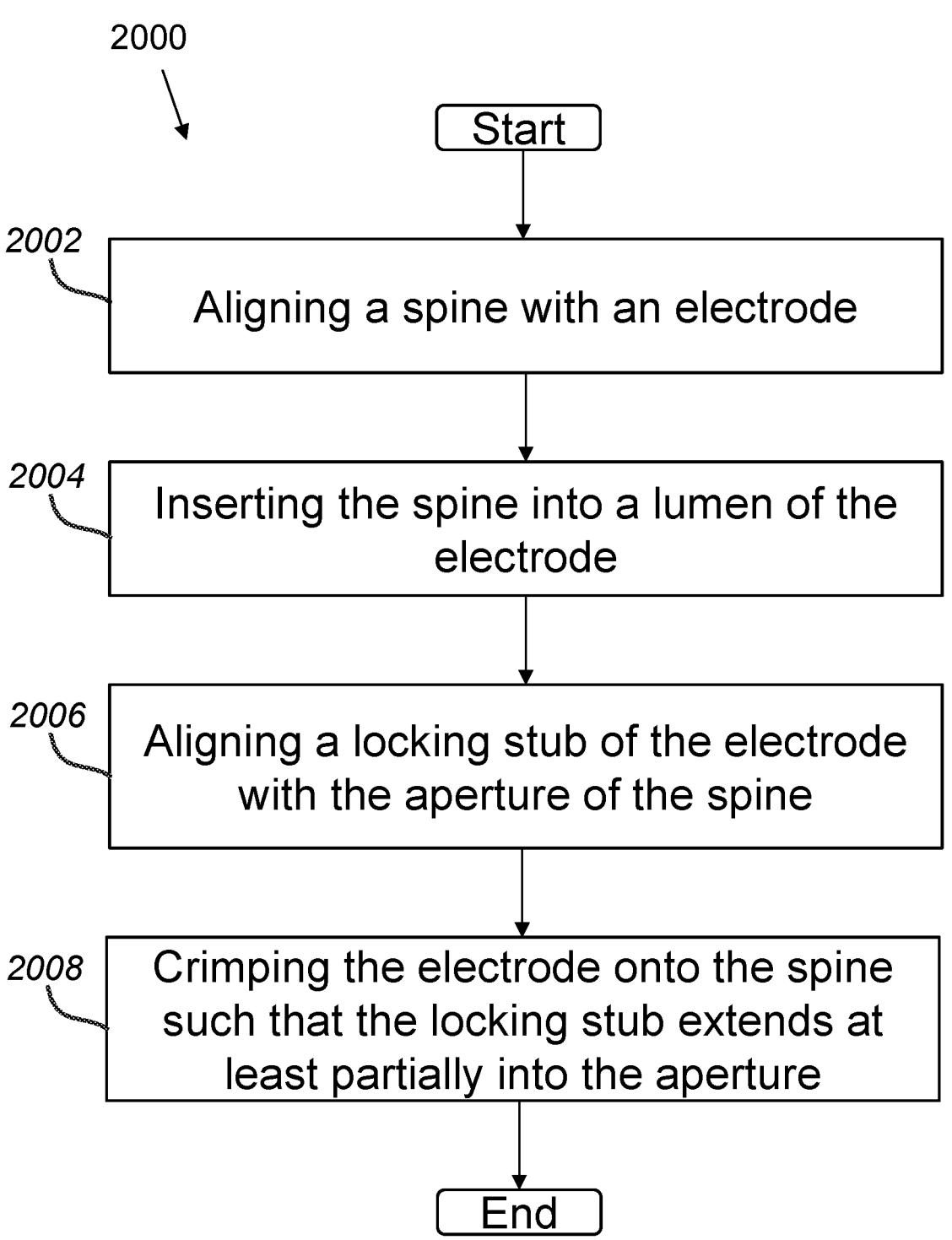
FIG. 20 is a flowchart illustrating a method of constructing a medical probe, in accordance with embodiments of the present disclosure.

FIG. 20 is a flowchart illustrating a method 2000 of constructing a medical probe 22, in accordance with embodiments of the present disclosure. The method 2000 can include aligning 2002 a spine (i.e., various spines 214) with an electrode (i.e., electrode 40). Aligning 2002 the spine with the electrode, for example, can include aligning the lumen of the electrode (i.e., first lumen 70) with the longitudinal axis of the spine. The method 2000 can include inserting 2004 the spine into a lumen of the electrode and aligning 2006 a locking stub (i.e., locking stub 80) with the aperture (i.e., various apertures 215) of the spine. The method can further include crimping 2008 the electrode onto the spine such that the locking stub extends at least partially into the aperture to secure the electrode to the spine. Crimping 2008 the electrode onto the spine can include using a handheld crimp tool, an electrical crimp tool, a hydraulic crimp tool, a pneumatic crimp tool, or other suitable crimping tool for the application. The method 2000 may optionally include aligning 2010 an electrically conductive member (e.g. a wire) of the medical probe 22 with a second lumen 78 of the electrode 40. The method 2000 may optionally include inserting 2012 the electrically conductive member into the second lumen 78. The method 2000 may optionally include coupling 2014 the electrically conductive member to the electrode 40 such that the electrically conductive member is in electrical communication with the electrode 40.

As will be appreciated by one skilled in the art, the method 2000 can include any of the various features of the disclosed technology described herein and can be varied depending on the particular configuration. For example, the method 2000 can further include inserting a wire into the second lumen 72 and electrically connecting the wire to the electrode 40. As another example, the method 2000 can include placing an electrically insulative material between the spine 214 and the electrode 40. Furthermore, the method 2000 can be repeated as many times as necessary to attach the appropriate number of electrodes 40 to the spine 214 for the particular application.

Figure 21:
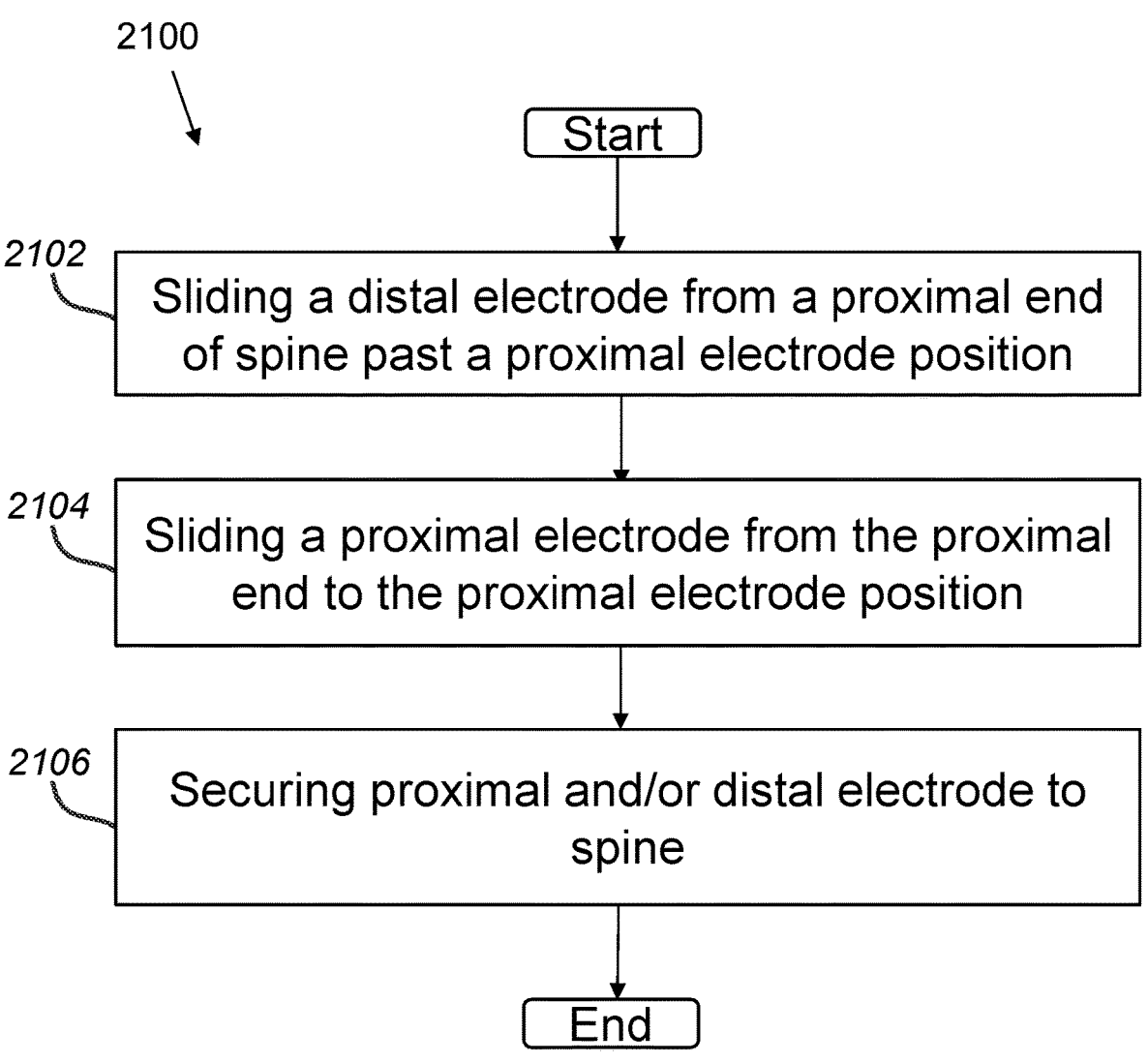
FIG. 21 is a flowchart illustrating a method of constructing a medical probe, in accordance with embodiments of the present disclosure.

FIG. 21 is a flowchart illustrating a method 2100 of constructing a spine 214 for a medical probe 22, in accordance with embodiments of the present disclosure. The method 2100 can include sliding 2102 distal electrode (e.g. distal electrode 40B) from a proximal end 216 of the spine 214 past a proximal electrode position (e.g., proximal electrode stop 220). The method 2100 can include sliding 2104 a proximal electrode 40A from the proximal end 216 to the proximal electrode position (e.g., at proximal electrode stop 220). The method may also optionally include securing 2106 the proximal and/or distal electrode (e.g., electrode 40A and 40B) to the spine 214.

As will be appreciated by one skilled in the art, the method 2100 can include any of the various features of the disclosed technology described herein and can be varied depending on the particular configuration. The embodiments described above are cited by way of example, and the present invention is not limited by what has been particularly shown and described hereinabove. Rather, the scope of the invention includes both combinations and sub combinations of the various features described hereinabove, as well as variations and modifications thereof which would occur to persons skilled in the art upon reading the foregoing description and which are not disclosed in the prior art.

In some examples, disclosed devices (e.g., spines, basket assemblies, electrodes, and/or medical probes) and methods may involve one or more of the following clauses:

Clause 1: A spine member for an end effector, the spine member extending along a longitudinal axis from a proximal end to a distal end, the spine member includes a unidirectional proximal stop member to allow an electrode to slide in a direction distally but not proximally and a distal stop member to prevent an electrode from sliding past.

Clause 2: An expandable basket assembly for a medical probe, comprising: a plurality of spines configured to bow radially outward from a central axis when the expandable basket assembly is transitioned from a collapsed form to an expanded form, each spine of the plurality of spines comprising: a proximal electrode stop configured to allow a distal electrode to slide distally on each spine past the proximal electrode stop but prevent a proximal electrode from sliding distally past the proximal electrode stop; and a distal electrode stop configured to prevent the distal electrode from sliding distally past the distal electrode stop.

Clause 3: The expandable basket assembly of clause 2, wherein the proximal electrode stop comprises: a pair of first proximal protrusions extending from opposing sides of each spine with a first proximal facing portion angled away from a proximal end of each spine and a first distal facing portion approximately parallel with the proximal end of each spine.

Clause 4: The expandable basket assembly of clauses 2 or 3, wherein the proximal electrode stop further comprises a pair of second proximal protrusions extending from the opposing sides of each spine with second proximal facing portion angled away from the proximal end of each spine.

Clause 5: The expandable basket assembly of clause 4, wherein the proximal electrode stop further comprises a bulged portion in a default state that is configured to retain an electrode in place in a default state and configured to allow an electrode to travel distally along each spine when the respective spine is deformed.

Clause 6: The expandable basket assembly of clause 2, wherein the proximal electrode stop comprises a first pair of lateral cutouts, a second pair of lateral cutouts, and a first coil, a second coil, the first pair of lateral cutouts configured to receive the first coil and the second pair of lateral cutouts configured to receive the second coil, the first and second coils configured to restrain the proximal electrode positioned therebetween from sliding distally or proximally after the distal electrode is positioned distally past the proximal electrode stop.

Clause 7: The expandable basket assembly of clause 6, wherein the distal electrode stop comprises a third pair of lateral cutouts, a fourth pair of lateral cutouts, and a third coil, a fourth coil, the third pair of lateral cutouts configured to receive the third coil and the fourth pair of lateral cutouts configured to receive the fourth coil, the third and fourth coils configured to restrain the distal electrode positioned therebetween from sliding distally or proximally.

Clause 8: The expandable basket assembly of clause 2, wherein the proximal electrode stop comprises a proximal diamond portion, a distal diamond portion, and a diamond intersection connected to the proximal and distal diamond portions.

Clause 9: The expandable basket assembly of clause 8, wherein: in a default state: the proximal diamond portion is configured to prevent the proximal electrode from sliding proximally, the distal diamond portion is configured to prevent the proximal electrode from sliding distally, and in an expanded state: the proximal diamond portion is configured to allow the distal electrode to slide distally, and the distal diamond portion is configured to allow the distal electrode to slide distally.

Clause 10: The expandable basket assembly of clause 2, wherein the proximal electrode stop comprises: a pair of proximal protrusions comprising a proximal face angled away from the proximal end of the spine and a distal face substantially parallel to the proximal end of the spine; and a distal aperture configured to receive a protrusion of a retainer rivet.

Clause 11: The expandable basket assembly of claim 10, wherein the retainer rivet comprises a polymer.

Clause 12: The expandable basket assembly of clause 3, wherein the proximal electrode stop further comprises: a shim distal to the pair of first proximal protrusions that is configured to insert into a lumen of the proximal electrode and prevent distal movement of the proximal electrode.

Clause 13: The expandable basket assembly of clause 2, wherein the proximal electrode stop comprises: a first shim that is configured to insert into a lumen of the proximal electrode and prevent proximal movement of the proximal electrode; and a second shim distal to the pair of first proximal protrusions that is configured to insert into the lumen of the proximal electrode and prevent distal movement of the proximal electrode.

Clause 14: The expandable basket assembly of clause 2, wherein: the proximal electrode stop comprises: a pair of first proximal protrusions extending from opposing sides of each spine with a first proximal facing portion angled away from a proximal end of each spine and a first distal facing portion approximately perpendicular with the proximal end of each spine; and the distal electrode stop comprises: a pair of distal protrusions extending from opposing sides of each spine with a proximal facing portion substantially perpendicular with the proximal end of each spine.

Clause 15: The expandable basket assembly of clause 14, further comprising a flexible member between the proximal electrode and the distal electrode.

Clause 16: The expandable basket assembly of clause 15, wherein the flexible member is configured to prevent proximal movement of the distal electrode and distal movement of the proximal electrode.

Clause 17: The expandable basket assembly of clause 2, wherein each spine has a first width at the proximal electrode stop and second width at the distal electrode stop, the second width is greater than the first width.

Clause 18: The expandable basket assembly of clause 17, wherein each spine gradually changes from the first width to the second width.

Clause 19: The expandable basket assembly of clause 18, further comprising the proximal electrode having a first lumen with a first diameter less than or equal to the first width such that it cannot move distally past the proximal electrode stop and the distal electrode having a second lumen with a second diameter greater than the first width but less than or equal to the second width such that it cannot move distally past the distal electrode stop when placed on each spine.

Clause 20: The expandable basket assembly of clause 18, further comprising: the proximal electrode having a first lumen gradually changing from a first diameter to a second diameter, the first diameter less than or equal to the first width and the second diameter is greater than the first diameter and less than or equal to the second width; and the distal electrode having a second lumen gradually changing from the second diameter to the first diameter.

Clause 21: The expandable basket assembly of clause 2, wherein each spine has: a first width at the proximal end for a first length extending away from the proximal end, a second width for a second length, the second width being greater than the first width, a third width for a third length, the third width being greater than the second width, the first width gradually increasing to the second width over a fourth length and the second width gradually increasing to the third width over a fifth length.

Clause 22: The expandable basket assembly of clause 2, wherein the proximal electrode stop comprises: a pair of first proximal arms extending from opposing sides of each spine angled away from the proximal end of each spine, the pair of arms are configured to close such that the distal electrode can slide over the pair of arms while also forming a pocket retaining the proximal electrode when the proximal electrode moves proximally.

Clause 23: The expandable basket assembly of clause 2, wherein each spine comprises a first portion configured to receive and connect with the proximal electrode and having a first width, a second portion having a second width, and a third portion having a third width and configured to receive and connect with the distal electrode, the second width being greater than the first and third width.

Clause 24: The expandable basket assembly of clause 2, wherein each spine of the plurality of spines comprising one or more apertures extending therethrough from a first side of the spine to a second side of the spine, the one or more apertures configured to receive a locking stub of the proximal or distal electrode such that when the proximal or distal electrode is mechanically coupled to the spine, the locking stub extends through the aperture preventing the proximal and distal electrode from sliding distally or proximally along the spine.

Clause 25: The expandable basket assembly of clause 2, further comprising the proximal and distal electrodes, each defining a lumen extending therethrough and a locking stub extending at least partially into the lumen.

Clause 26: The expandable basket assembly of clause 25, wherein each spine of the plurality of spines passing through a lumen of the proximal and distal electrodes.

Clause 27: An expandable basket assembly for a medical probe, comprising: a plurality of electrodes; a plurality of spines configured to bow radially outward from a central axis when the expandable basket assembly is transitioned from a collapsed form to an expanded form, each spine of the plurality of spines comprising a plurality of electrode extension portions extending radially from each spine, each electrode extension portion comprises a band to receive and retain an electrode of the plurality of electrodes.

Clause 28: The expandable basket assembly of clause 27, wherein the plurality of electrodes comprise platinum.

Clause 29: The expandable basket assembly of clause 27, wherein the plurality of electrode extension portions have an adjustable height.

Clause 30: A method of constructing a medical probe, the method comprising: aligning a spine of an expandable basket assembly with an electrode of the expandable basket assembly, the spine comprising a proximal end, a distal end, and an aperture extending therethrough; inserting the spine into a lumen of the electrode; aligning a locking stub of the electrode with the aperture; and crimping the electrode onto the spine such that the locking stub extends at least partially into the aperture to prevent the electrode from sliding proximally or distally along the spine.

Clause 31: The method according to clause 30, the spine further comprising an insulative material configured to electrically isolate the spine from the electrode.

Clause 32: The method according to clause 30, wherein the expandable basket assembly further comprises an insulative material disposed between the electrode and the spine to electrically isolate the electrode from the spine.

Clause 33: The method according to clause 30, wherein the lumen comprises a first lumen, the method further comprising: aligning an electrically conductive member of the medical probe with a second lumen of the electrode; inserting the electrically conductive member into the second lumen; and coupling the electrically conductive member to the electrode such that the electrically conductive member is in electrical communication with the electrode.

Clause 34: The method according to clause 33, wherein the electrically conductive member is insulated from the spine.

Clause 35: The method according to clause 30, wherein an interface between the locking stub of the electrode and the spine at the aperture comprises an interference fitting.

Clause 36: The method according to clause 30, wherein the spine comprises a material selected from a group consisting of nitinol, cobalt chromium, stainless steel, titanium.

Clause 37: The method according to clause 30, wherein the spine comprises a polymer material.

Clause 38: The method according to clause 30, wherein the aperture of the spine comprises a first aperture, the spine further comprising a second aperture, the method further comprising: aligning the spine with a second electrode of the expandable basket assembly; inserting the spine into a lumen of the second electrode; aligning a locking stub of the second electrode with the second aperture; and crimping the second electrode onto the spine such that the locking stub extends at least partially into the second aperture to prevent the second electrode from sliding proximally or distally along the spine.

Clause 39: A method of constructing a medical probe, the method comprising: sliding a distal electrode from a proximal end of a spine past a proximal electrode position; sliding a proximal electrode from the proximal end to the proximal electrode position; and securing the proximal and distal electrode to the spine.

What is claimed is:

1. An expandable basket assembly for a medical probe, comprising:
   a plurality of spines configured to bow radially outward from a central axis when the expandable basket assembly is transitioned from a collapsed form to an expanded form, each spine of the plurality of spines comprising:
   a proximal electrode stop configured to allow a distal electrode to slide distally on each spine past the proximal electrode stop but prevent a proximal electrode from sliding distally past the proximal electrode stop; and
   a distal electrode stop configured to prevent the distal electrode from sliding distally past the distal electrode stop.

2. The expandable basket assembly of claim 1, wherein the proximal electrode stop comprises:
   a pair of first proximal protrusions extending from opposing sides of each spine with a first proximal facing portion angled away from a proximal end of each spine and a first distal facing portion approximately parallel with the proximal end of each spine.

3. The expandable basket assembly of claim 2, wherein the proximal electrode stop further comprises a pair of second proximal protrusions extending from the opposing sides of each spine with second proximal facing portion angled away from the proximal end of each spine.

4. The expandable basket assembly of claim 3, wherein the proximal electrode stop further comprises a bulged portion in a default state that is configured to retain an electrode in place in a default state and configured to allow an electrode to travel distally along each spine when the respective spine is deformed.

5. The expandable basket assembly of claim 1, wherein the proximal electrode stop comprises a first pair of lateral cutouts, a second pair of lateral cutouts, and a first coil, a second coil, the first pair of lateral cutouts configured to receive the first coil and the second pair of lateral cutouts configured to receive the second coil, the first and second coils configured to restrain the proximal electrode positioned therebetween from sliding distally or proximally after the distal electrode is positioned distally past the proximal electrode stop.

6. The expandable basket assembly of claim 5, wherein the distal electrode stop comprises a third pair of lateral cutouts, a fourth pair of lateral cutouts, and a third coil, a fourth coil, the third pair of lateral cutouts configured to receive the third coil and the fourth pair of lateral cutouts configured to receive the fourth coil, the third and fourth coils configured to restrain the distal electrode positioned therebetween from sliding distally or proximally.

7. The expandable basket assembly of claim 1, wherein the proximal electrode stop comprises a proximal diamond portion, a distal diamond portion, and a diamond intersection connected to the proximal and distal diamond portions.

8. The expandable basket assembly of claim 7, wherein:
   in a default state:
   the proximal diamond portion is configured to prevent the proximal electrode from sliding proximally,
   the distal diamond portion is configured to prevent the proximal electrode from sliding distally, and
   in an expanded state:
   the proximal diamond portion is configured to allow the distal electrode to slide distally, and
   the distal diamond portion is configured to allow the distal electrode to slide distally.

9. The expandable basket assembly of claim 1, wherein the proximal electrode stop comprises:
   a pair of proximal protrusions comprising a proximal face angled away from the proximal end of the spine and a distal face substantially parallel to the proximal end of the spine; and
   a distal aperture configured to receive a protrusion of a retainer rivet.

10. The expandable basket assembly of claim 1, wherein the proximal electrode stop comprises:
   a first shim that is configured to insert into a lumen of the proximal electrode and prevent proximal movement of the proximal electrode; and
   a second shim distal to the pair of first proximal protrusions that is configured to insert into the lumen of the proximal electrode and prevent distal movement of the proximal electrode.

11. The expandable basket assembly of claim 1, wherein:
   the proximal electrode stop comprises:
   a pair of first proximal protrusions extending from opposing sides of each spine with a first proximal facing portion angled away from a proximal end of each spine and a first distal facing portion approximately perpendicular with the proximal end of each spine; and the distal electrode stop comprises:

a pair of distal protrusions extending from opposing sides of each spine with a proximal facing portion substantially perpendicular with the proximal end of each spine.

12. The expandable basket assembly of claim 11, further comprising a flexible member between the proximal electrode and the distal electrode.

13. The expandable basket assembly of claim 1, wherein each spine has a first width at the proximal electrode stop and second width at the distal electrode stop, the second width is greater than the first width.

14. The expandable basket assembly of claim 13, further comprising the proximal electrode having a first lumen with a first diameter less than or equal to the first width such that it cannot move distally past the proximal electrode stop and the distal electrode having a second lumen with a second diameter greater than the first width but less than or equal to the second width such that it cannot move distally past the distal electrode stop when placed on each spine.

15. The expandable basket assembly of claim 13, further comprising:

the proximal electrode having a first lumen gradually changing from a first diameter to a second diameter, the first diameter less than or equal to the first width and the second diameter is greater than the first diameter and less than or equal to the second width; and the distal electrode having a second lumen gradually changing from the second diameter to the first diameter.

16. The expandable basket assembly of claim 1, wherein each spine has:

a first width at the proximal end for a first length extending away from the proximal end, a second width for a second length, the second width being greater than the first width, a third width for a third length, the third width being greater than the second width, the first width gradually increasing to the second width over a fourth length and the second width gradually increasing to the third width over a fifth length.

17. The expandable basket assembly of claim 1, wherein the proximal electrode stop comprises:

a pair of first proximal arms extending from opposing sides of each spine angled away from the proximal end of each spine, the pair of arms are configured to close such that the distal electrode can slide over the pair of arms while also forming a pocket retaining the proximal electrode when the proximal electrode moves proximally.

18. The expandable basket assembly of claim 1, wherein each spine comprises a first portion configured to receive and connect with the proximal electrode and having a first width, a second portion having a second width, and a third portion having a third width and configured to receive and connect with the distal electrode, the second width being greater than the first and third width.

19. An expandable basket assembly for a medical probe, comprising:

a plurality of electrodes;

a plurality of spines configured to bow radially outward from a central axis when the expandable basket assembly is transitioned from a collapsed form to an expanded form, each spine of the plurality of spines comprising a plurality of electrode extension portions extending radially from each spine, each electrode extension portion comprises a band to receive and retain an electrode of the plurality of electrodes, wherein the plurality of electrode extension portions have an adjustable height.

* * * * *